(12) United States Patent
Adams et al.

(10) Patent No.: US 12,274,440 B1
(45) Date of Patent: Apr. 15, 2025

(54) MOTOR OPTIMIZATION BY MINIMIZATION OF PARASITIC LOSSES AND TUNING MOTOR DRIVE CONFIGURATION

(71) Applicant: Cilag GmbH International, Zug (CH)

(72) Inventors: Shane R. Adams, Lebanon, OH (US); Frederick E. Shelton, IV, Hillsboro, OH (US); Matthew D. Cowperthwait, Cincinnati, OH (US); Nicholas J. Ross, Franklin, OH (US); Kevin M. Fiebig, Cincinnati, OH (US); Eric B. LaFay, Madeira, OH (US)

(73) Assignee: Cilag GmbH International?, Zug (CH)

( * ) Notice: Subject to any disclaimer, the term of this patent is extended or adjusted under 35 U.S.C. 154(b) by 0 days.

(21) Appl. No.: 18/379,771

(22) Filed: Oct. 13, 2023

(51) Int. Cl.
*A61B 17/064* (2006.01)
*A61B 17/072* (2006.01)
*A61B 17/00* (2006.01)

(52) U.S. Cl.
CPC .. *A61B 17/072* (2013.01); *A61B 2017/00017* (2013.01); *A61B 2017/00398* (2013.01); *A61B 2017/07271* (2013.01)

(58) Field of Classification Search
CPC .................................................. A61B 17/072
See application file for complete search history.

(56) References Cited

U.S. PATENT DOCUMENTS

| | | | |
|---|---|---|---|
| 9,005,199 B2 | 4/2015 | Beckman et al. | |
| 9,072,535 B2 | 7/2015 | Shelton, IV et al. | |
| 9,931,118 B2 | 4/2018 | Shelton, IV et al. | |
| 10,835,245 B2 | 11/2020 | Swayze et al. | |
| 11,576,677 B2 | 2/2023 | Shelton, IV et al. | |
| 2018/0168622 A1* | 6/2018 | Shelton, IV | A61B 17/07207 |
| 2019/0201023 A1* | 7/2019 | Shelton, IV | G16H 30/20 |
| 2019/0201027 A1* | 7/2019 | Shelton, IV | A61B 17/320068 |
| 2019/0201029 A1* | 7/2019 | Shelton, IV | A61B 17/07207 |
| 2019/0206565 A1* | 7/2019 | Shelton, IV | A61B 90/90 |
| 2020/0405415 A1 | 12/2020 | Shelton, IV et al. | |

OTHER PUBLICATIONS

IEEE Std 802.3-2012 (Revision of IEEE Std 802.3-2008), published Dec. 28, 2012.
"ATM-MPLS Network Interworking 2.0", published Aug. 2001.

* cited by examiner

*Primary Examiner* — Eyamindae C Jallow

(57) ABSTRACT

A powered surgical instrument disclosed. The instrument includes a first circuit portion operable at a first voltage level, a second circuit portion operable at a second voltage level, a voltage source to supply the first voltage level to supply power to electrical components in the first circuit portion; a transistor comprising a control terminal, a first conduction terminal, and a second conduction terminal, and a control circuit coupled to the control terminal of the transistor. The second voltage level is different from the first voltage level. The first conduction terminal is coupled to the voltage source. The control circuit is to set the transistor in a linear mode and control the transistor to set a current for operating the motor.

20 Claims, 9 Drawing Sheets t0 = firing begins
t1 = delay in Compensation
t2 = firing stops
t3 = voltage sag recovery ——— Uncompensated Voltage
·········· Compensation Factor
- - - Compensated Voltage

MOTOR OPTIMIZATION BY MINIMIZATION OF PARASITIC LOSSES AND TUNING MOTOR DRIVE CONFIGURATION

TECHNICAL FIELD

The present disclosure is directed to surgical instruments and, in various arrangements, to surgical stapling and cutting instruments and staple cartridges for use therewith that are configured to staple and cut tissue.

SUMMARY

The present disclosure provides a powered surgical instrument. The powered surgical instrument comprises a first circuit portion operable at a first voltage level, a second circuit portion operable at a second voltage level. The second voltage level is different from the first voltage level. The powered surgical instrument further comprises a voltage source to supply the first voltage level to supply power to electrical components in the first circuit portion and a transistor. The transistor comprises a control terminal, a first conduction terminal, and a second conduction terminal. The first conduction terminal is coupled to the voltage source. The powered surgical instrument further comprises a control circuit coupled to the control terminal of the transistor. The control circuit to set the transistor in a linear mode and control the transistor to set a current for operating the motor.

The present disclosure provides a method comprising providing, by a voltage source, a first voltage level to a first circuit portion, setting, by a control circuit, a transistor in a linear mode, controlling, by the control circuit, the transistor to set a second voltage level to power in a second circuit portion a motor. The second voltage level is different from the first voltage level. The method further comprises setting, by the control circuit, a current for the motor.

The present disclosure provides a powered surgical instrument, comprising a motor, a first circuit portion operable at a first voltage level, a second circuit portion operable at a second voltage level. The second voltage level is different from the first voltage level. The powered surgical instrument further comprises a voltage source to supply the first voltage level to power electrical components in the first circuit portion, a transistor coupled to the voltage source and the motor, and a control circuit coupled to the transistor. The control circuit is to control the transistor to set the second voltage level to supply power to the motor in the second circuit portion and control the transistor to set a current to the motor based on a torque of the motor.

LISTING OF THE FIGURES

In the description, for purposes of explanation and not limitation, specific details are set forth, such as particular aspects, procedures, techniques, etc. to provide a thorough understanding of the present technology. However, it will be apparent to one skilled in the art that the present technology may be practiced in other aspects that depart from these specific details.

The accompanying drawings, where like reference numerals refer to identical or functionally similar elements throughout the separate views, together with the detailed description below, are incorporated in and form part of the specification, and serve to further illustrate aspects of concepts that include the claimed disclosure and explain various principles and advantages of those aspects.

The methods, devices, and systems disclosed herein have been represented where appropriate by conventional symbols in the drawings, showing only those specific details that are pertinent to understanding the various aspects of the present disclosure so as not to obscure the disclosure with details that will be readily apparent to those of ordinary skill in the art having the benefit of the description herein.

DESCRIPTION

Figure 1:
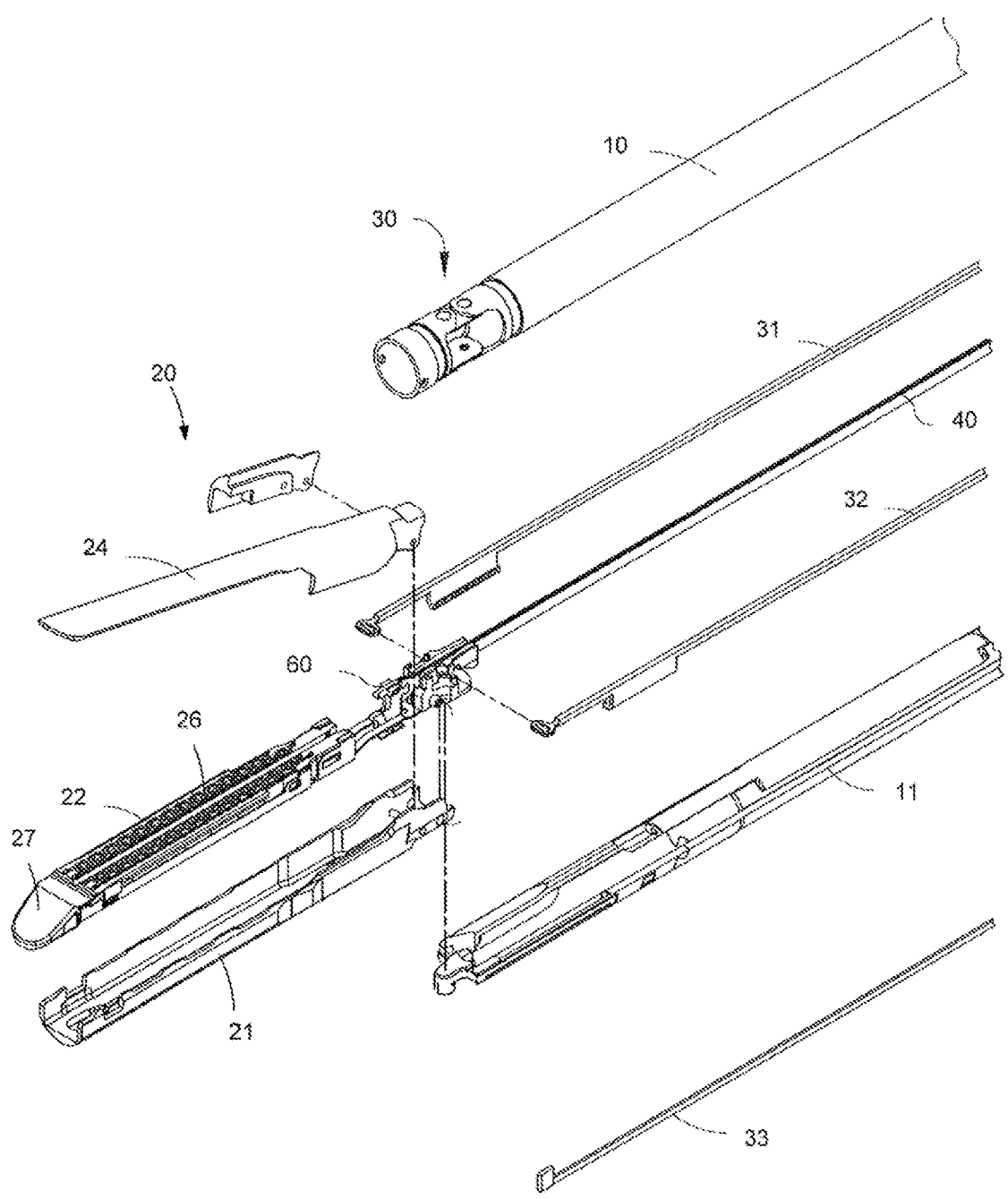
FIG. 1 illustrates an exploded view of an end effector and a shaft portion of a powered surgical stapler, in accordance with the present disclosure.

Applicant of the present application owns the following U.S. Patent Applications that were filed on Oct. 13, 2023 and which are each herein incorporated by reference in their respective entireties:

U.S. patent application Ser. No. 18/379,759, titled METHOD OF OPERATING A SURGICAL STAPLING INSTRUMENT;

U.S. patent application Ser. No. 18/379,762, titled SURGICAL STAPLING SYSTEMS WITH ADAPTIVE STAPLE FIRING ALGORITHMS;

U.S. patent application Ser. No. 18/379,763, titled LEARNED TRIGGERS FOR ADAPTIVE CONTROL OF SURGICAL STAPLING SYSTEMS;

U.S. patent application Ser. No. 18/379,766, titled CONTROL CIRCUIT FOR ACTUATING MOTORIZED FUNCTION OF SURGICAL STAPLING INSTRUMENT UTILIZING INERTIAL DRIVE TRAIN PROPERTIES;

U.S. patent application Ser. No. 18/379,768, titled PROPORTIONATE BALANCING OF THE FUNCTION

IMPACT MAGNITUDE OF BATTERY OUTPUT TO PEAK MOTOR CURRENT;

U.S. patent application Ser. No. 18/379,773, titled APPARATUS AND METHOD TO REDUCE PARASITIC LOSSES OF THE ELECTRICAL SYSTEM OF A SURGICAL INSTRUMENT;

U.S. patent application Ser. No. 18/379,776, titled SURGICAL TOOL WITH RELAXED FLEX CIRCUIT ARTICULATION;

U.S. patent application Ser. No. 18/379,777, titled WIRING HARNESS FOR SMART STAPLER WITH MULTI AXIS ARTICULATION;

U.S. patent application Ser. No. 18/379,781, titled SURGICAL SYSTEM WITH WIRELESS ARRAY FOR POWER AND DATA TRANSFER; and U.S. patent application Ser. No. 18/379,784, titled SURGICAL STAPLE CARTRIDGE COMPRISING REPLACEABLE ELECTRONICS PACKAGE; now U.S. Pat. No. 12,193,670.

Applicant of the present application owns the following U.S. Patent Applications that were filed on Oct. 13, 2023 and which are each herein incorporated by reference in their respective entireties:

U.S. patent application Ser. No. 18/379,790, titled METHOD OF ASSEMBLING A STAPLE CARTRIDGE;

U.S. patent application Ser. No. 18/379,793, titled CONTROL SURFACES ON A STAPLE DRIVER OF A SURGICAL STAPLE CARTRIDGE;

U.S. patent application Ser. No. 18/379,796, titled INTEGRAL CARTRIDGE STIFFENING FEATURES TO REDUCE CARTRIDGE DEFLECTION;

U.S. patent application Ser. No. 18/379,801, titled STAPLE CARTRIDGE COMPRISING WALL STRUCTURES TO REDUCE CARTRIDGE DEFLECTION;

U.S. patent application Ser. No. 18/379,803, titled PAN-LESS STAPLE CARTRIDGE ASSEMBLY COMPRISING RETENTION FEATURES FOR HOLDING STAPLE DRIVERS AND SLED;

U.S. patent application Ser. No. 18/379,805, titled STAPLE CARTRIDGE COMPRISING A SLED HAVING A DRIVER LIFT CAM;

U.S. patent application Ser. No. 18/379,808, titled SURGICAL STAPLE CARTRIDGES WITH SLEDS CONFIGURED TO BE COUPLED TO A FIRING DRIVER OF A COMPATIBLE SURGICAL STAPLER;

U.S. patent application Ser. No. 18/379,810, titled STAPLE CARTRIDGE COMPRISING A COMPOSITE SLED;

U.S. patent application Ser. No. 18/379,811, titled SURGICAL INSTRUMENTS WITH JAW AND FIRING ACTUATOR LOCKOUT ARRANGEMENTS LOCATED PROXIMAL TO A JAW PIVOT LOCATION;

U.S. patent application Ser. No. 18/379,815, titled SURGICAL INSTRUMENTS WITH LATERALLY ENGAGEABLE LOCKING ARRANGEMENTS FOR LOCKING A FIRING ACTUATOR;

U.S. patent application Ser. No. 18/379,817, titled DUAL INDEPENDENT KEYED LOCKING MEMBERS ACTING ON THE SAME DRIVE MEMBER;

U.S. patent application Ser. No. 18/379,820, titled ADJUNCTS FOR USE WITH SURGICAL STAPLING INSTRUMENTS;

U.S. patent application Ser. No. 18/379,822, titled ADJUNCTS FOR USE WITH SURGICAL STAPLING INSTRUMENTS;

U.S. patent application Ser. No. 18/379,826, titled JAW CONTROL SURFACES ON A SURGICAL INSTRUMENT JAW;

U.S. patent application Ser. No. 18/379,827, titled ZONED ALGORITHM ADAPTIVE CHANGES BASED ON CORRELATION OF COOPERATIVE COMPRESSION CONTRIBUTIONS OF TISSUE;

U.S. patent application Ser. No. 18/379,831, titled STAPLE CARTRIDGES COMPRISING TRACE RETENTION FEATURES; and U.S. patent application Ser. No. 18/379,832, titled STAPLE CARTRIDGES COMPRISING STAPLE RETENTION FEATURES.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the described and illustrated embodiments are non-limiting examples, and thus it can be appreciated that the specific structural and functional details disclosed herein may be representative and illustrative. Variations and changes may be made without departing from the scope of the claims.

Various methods, instruments, and systems are provided for performing surgical procedures. Various surgical systems disclosed herein include working portions that can be inserted into a body in any way, such as through a natural orifice, through an incision or puncture hole formed in tissue, etc. The working portions or end effector portions can be inserted directly into a patient's body or can be inserted through an access device that has a working channel. As the present Detailed Description proceeds, it will be understood that the various unique and novel arrangements of the various forms of surgical systems disclosed herein may be effectively employed in connection with robotically-controlled surgical systems and/or hand-held surgical systems. Various robotic systems, instruments, components and methods are disclosed in U.S. patent application Ser. No. 13/118,241, entitled SURGICAL STAPLING INSTRUMENTS WITH ROTATABLE STAPLE DEPLOYMENT ARRANGEMENTS, which is incorporated by reference herein in its entirety.

Figure 2:
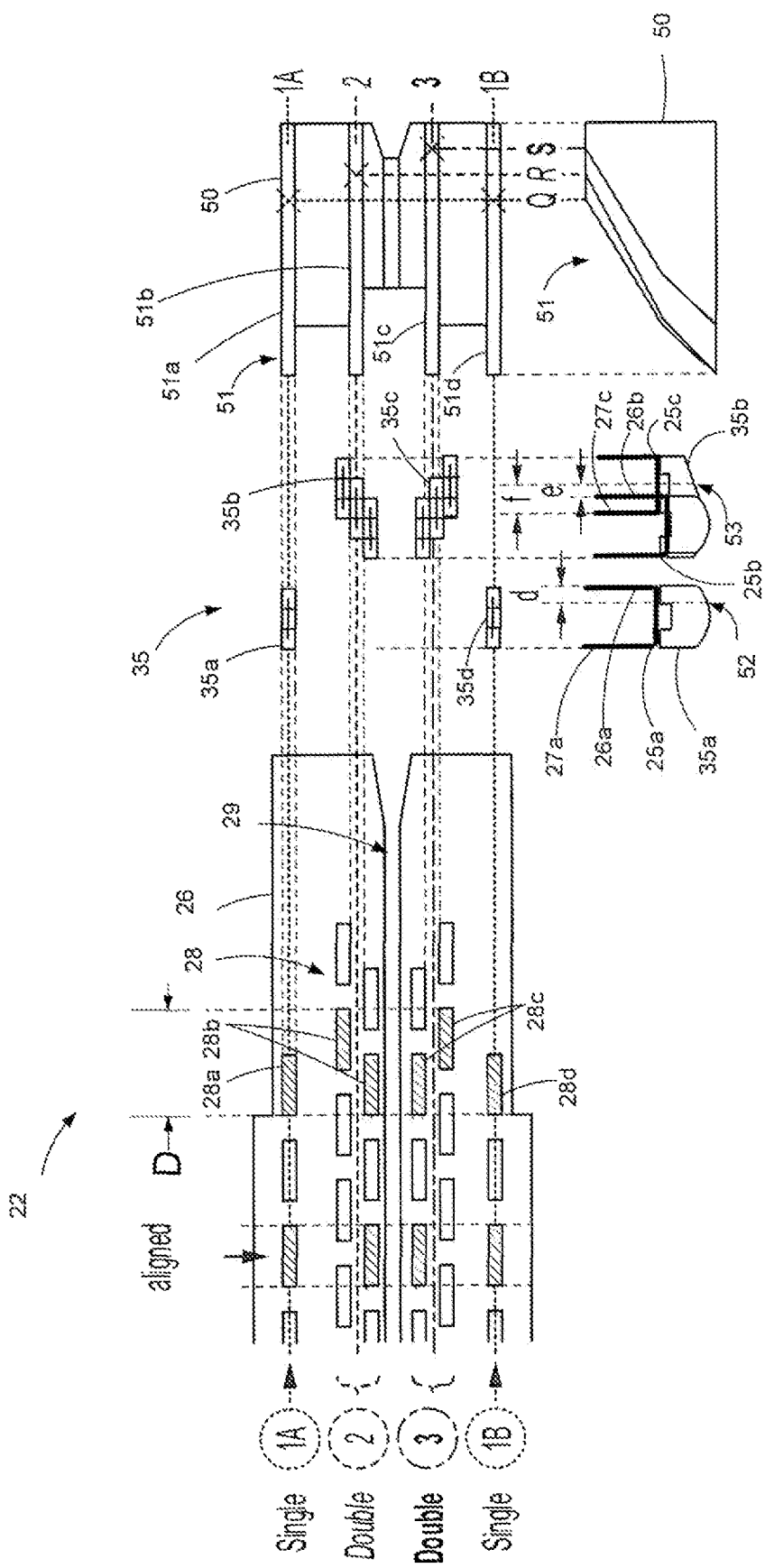
FIG. 2 is a diagram illustrating components of a staple cartridge, in accordance with the present disclosure.
Figure 3:
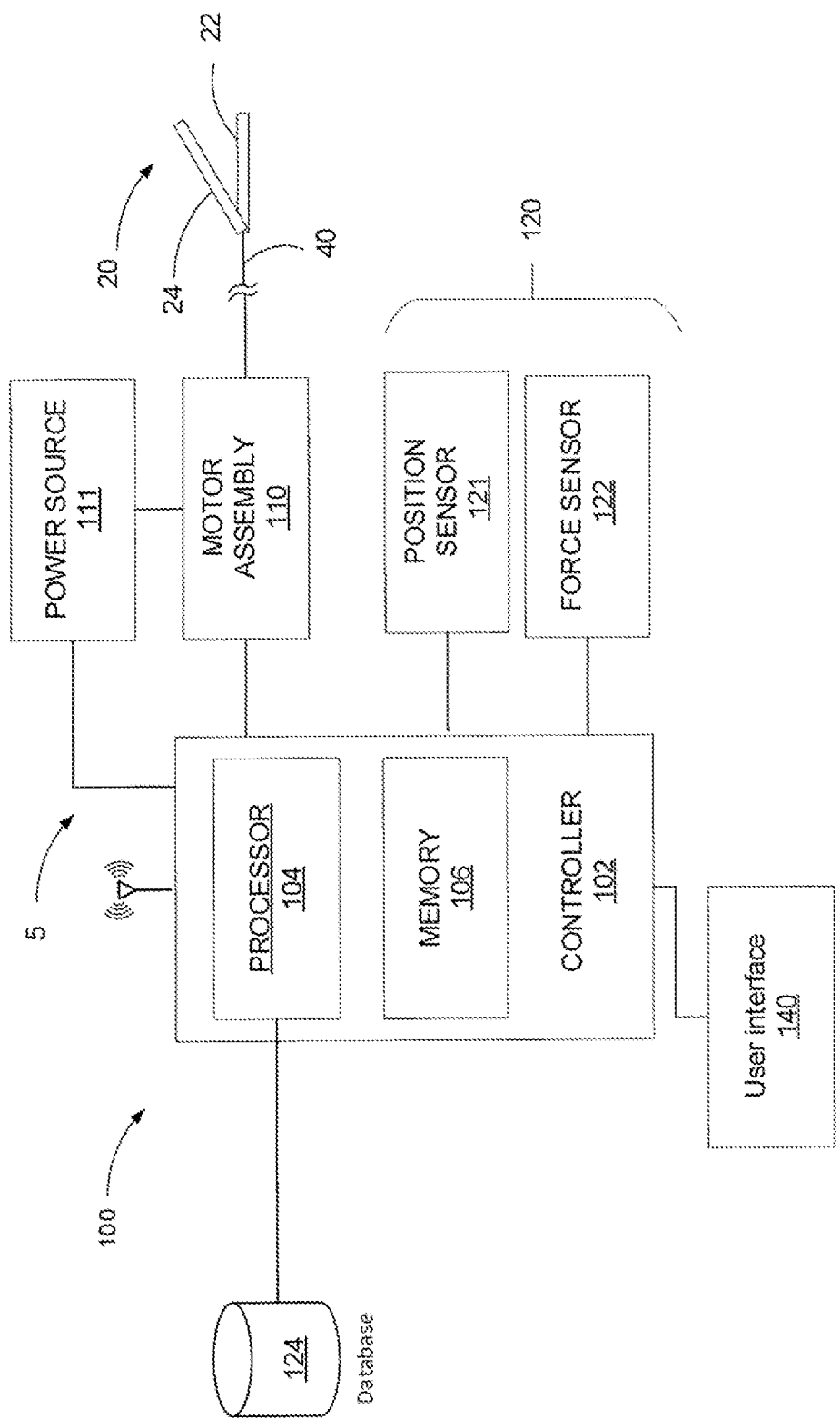
FIG. 3 is a diagram illustrating various components of a powered surgical stapler, in accordance with the present disclosure.

Referring to FIGS. 1-3, a powered surgical stapling instrument 5 includes a shaft 10 and an end effector 20 extending from the shaft 10. The end effector 20 includes a first jaw and a second jaw. The first jaw defines a channel 21 and a staple cartridge 22 removably positionable in the channel 21. However, other embodiments are envisioned in which a staple cartridge is not removable, or at least readily replaceable, from the first jaw. The second jaw includes an anvil 24 configured to deform the staples 25 (See FIG. 2) ejected from the staple cartridge 22. The second jaw is pivotable relative to the first jaw about a closure axis to transition the end effector 20 between an open configuration and a closed configuration. Other embodiments are envisioned in which the first jaw is pivotable relative to the second jaw.

The powered surgical stapling instrument 5 further includes an articulation joint 30 configured to permit the end effector 20 to be rotated, or articulated, relative to the shaft 10. The end effector 20 is rotatable about an articulation axis extending through the articulation joint 30. Other embodiments are envisioned which do not include an articulation joint. In the illustrated example, cooperating articulation rods 31, 32 are configured to articulate the end effector 20 relative to the shaft 10 about an articulation joint 30. The powered surgical stapling instrument 5 further includes an articulation lock bar 33 the selectively prevents the articulation of the end effector 20.

The staple cartridge 22 includes a cartridge body 27 with a proximal end, a distal end, and a deck 26 extending between the proximal end and the distal end. In use, the staple cartridge 22 is positioned on a first side of the tissue to be stapled and the anvil 24 is positioned on a second side of the tissue. In accordance with the present disclosure, the anvil 24 can be moved toward the staple cartridge 22 to compress and clamp the tissue against the deck 26. In other embodiments, the staple cartridge 22 can be moved relative to the anvil 24 or, alternatively, both the staple cartridge 22 and the anvil 24 can be moved to compress and clamp the tissue.

Further to the above, a drive shaft 40 is movable distally to motivate a firing beam 60 to transition the end effector 20 toward the closed configuration, thereby compressing the tissue. In the illustrated example, the firing beam 60 is in the form of an I-beam that includes a first cam and a second cam configured to engage the first and second jaws, respectively. As the firing beam 60 is advanced distally, the first cam and the second cam can control the distance, or tissue gap, between the deck of the staple cartridge 22 and the anvil 24. In the illustrated example, the firing beam 60 motivates a sled 50 to deploy the staples 25 from the staple cartridge 22. A separate closure mechanism, e.g., a closure tube, may be employed to transition the end effector 20 toward the closed configuration. Additionally, in accordance with the present disclosure, the firing beam 60 may or may not include the first and second cams. The firing beam 60 may be in the form of an E-beam with first, second, and third cams. The firing beam 60 and the closure tube can cooperatively effect closure of the end effector 20. Further, in accordance with the present disclosure, the firing beam 60 may only effect deployment of the staples 25.

In accordance with the present disclosure, as illustrated in FIG. 1, the firing beam 60 can include a knife configured to incise the tissue captured intermediate the staple cartridge 22 and the anvil 24. It is desirable for the knife to be positioned at least partially proximal to the ramped surfaces such that the staples are ejected ahead of the knife. More details about alternative embodiments of surgical stapling systems, suitable for use with the present disclosure, are disclosed in U.S. patent application Ser. No. 15/385,887 entitled METHOD FOR ATTACHING A SHAFT ASSEMBLY TO A SURGICAL INSTRUMENT AND, ALTERNATIVELY, TO A SURGICAL ROBOT, and U.S. patent application Ser. No. 16/209,416, entitled METHOD OF HUB COMMUNICATION, PROCESSING, DISPLAY, AND CLOUD ANALYTICS, which are hereby incorporated by reference herein in their entireties.

The staples 25 removably stored in the cartridge body 27 can be deployed into the tissue. The cartridge body 27 includes staple cavities 28 defined therein wherein staples 25 are removably stored in the staple cavities 28. The staple cavities 28 are arranged in longitudinal rows. In the illustrated example, three rows of staple cavities 28 are positioned on a first side of a longitudinal slot 29 and three rows of staple cavities 28 are positioned on a second side of the longitudinal slot. Other arrangements of staple cavities 28 and staples 25 are possible.

The staples 25 are supported by staple drivers 35 in the cartridge body 27. The staple drivers 35 are movable between a first, or unfired position, and a second, or fired, position to eject the staples 25 from the staple cavities 28. The staple drivers 35 are movable between their unfired positions and their fired positions by a sled 50 that includes ramped surfaces 51 configured to slide under the staple drivers 35 and lift the staple drivers 35, and the staples 25 supported thereon, toward the anvil 24. In the illustrated example, the distal movement of the drive shaft 40 causes the sled 50 to move distally within the staple cartridge 22 to deploy the staples 25.

Referring primarily to FIG. 2, the sled 50 includes a first ramped surface 51a, a second ramped surface 51b, a third ramped surface 51c, and a fourth ramped surface 51d configured to engage a first staple drive 35a, a second staple driver 35b, a third staple driver 35c, and a fourth staple driver 35d, respectively, along a staple-forming distance (D) to deploy staples 25 from corresponding staple cavities 28a, 28b, 28c, 28d for forming against corresponding forming pockets in the anvil 24. In the illustrated example, the staple drivers 35b, 35c are double drivers, while the staple drivers 35a, 35d are single drivers. Double drivers support two staples in two separate staple cavities, while single drivers support a single staple in a single staple cavity.

FIG. 3 is a block diagram illustrating one exemplification of the powered surgical stapling instrument 5. Various components of the surgical stapling instrument 5 communicate with a control circuit 100. Such components may receive signals from and/or transmit signals to the control circuit 100. Such signals include command signals, status signals, sensor signals, and/or any other suitable signals. The control circuit 100 can be configured to implement various methods described herein with the aid of various components of the surgical stapling system in communication with the control circuit 100. In the illustrated example, the control circuit 100 includes a controller 102 comprising one or more processors 104 (e.g., microprocessor, microcontroller) coupled to at least one memory circuit 106. The memory circuit 106 stores machine executable instructions that when executed by the processor 104, cause the processor 104 to execute machine instructions to implement various processes described herein. The processor 104 may be any one of a number of single or multi-core processors known in the art. The memory circuit 106 may comprise volatile and non-volatile storage media. The processor 104 may include an instruction processing unit and an arithmetic unit. The instruction processing unit may be configured to receive instructions from the memory circuit 106. In accordance with the present disclosure, the control circuit 100 may include a combinational logic circuit and/or a sequential logic circuit. The processor 104 is in communication with a database 124 to store various information associated with the powered surgical stapling instrument 5. In accordance with the present disclosure, the database 124 can store and identifier of a staple cartridge, or other component of the end effector 20.

In accordance with the present disclosure, the control circuit 100 can be configured to communicate with a motor assembly 110 that includes a motor and a motor controller, for example. The motor assembly may generate rotational motion to effect a translating motion of the drive shaft 40. The control circuit 160 may generate a motor set point signal. The motor set point signal may be provided to a motor controller. The motor controller may comprise one or more circuits configured to provide a motor drive signal to a motor to drive the motor as described herein. The motor may be a brushed DC electric motor. For example, the velocity of the motor may be proportional to the motor drive signal. Alternatively, or additionally, the motor may be a brushless DC electric motor and the motor drive signal may comprise a PWM signal provided to one or more stator windings of the motor. Also, in accordance with the present disclosure, the motor controller may be omitted, and the control circuit 100 may generate the motor drive signal directly. The position, movement, displacement, and/or translation of the drive shaft 40, the firing beam 60 and/or the sled 50 (collectively referred to herein as the "firing assembly") can be measured/monitored by the control circuit 100 based on input from one or more sensors 120.

The motor assembly 110 may be powered by a power source 111 that in one form may comprise a removable power pack. The power pack may include a housing configured to support a plurality of batteries that may each include, for example, a Lithium Ion ("LI") or other suitable battery, and may be connected in series, for example. The power source 111 may be replaceable and/or rechargeable. Other power sources are contemplated by the present disclosure.

The sensors 120 may include a position sensor 121 configured to sense a position, movement, displacement, and/or translation of one or more components of the firing assembly such as, for example, the drive shaft 40, the firing beam 60 and/or the sled 50. The position sensor 121 may include any type of sensor that is capable of generating position data that indicate a position of the firing assembly. In accordance with the present disclosure, the position sensor 121 may include an encoder configured to provide a series of pulses to the control circuit 100 as the firing assembly translates distally and proximally. The control circuit 100 may track the pulses to determine the position, movement, displacement, and/or translation of the components of the firing assembly. Other suitable position sensors may be used, including, for example, a proximity sensor. Other types of position sensors may provide other signals indicating motion of the firing assembly. Where the motor is a stepper motor, the control circuit 100 may track the position of components of the firing assembly by aggregating the number and direction of steps that the motor has been instructed to execute. The sensors 120 may be located in the end effector 20 or at any other portion of the powered surgical stapling instrument 5.

Various sensors 120 may be adapted to measure various other parameters such as gap distance versus time, tissue compression versus time, and anvil strain versus time. The sensors 120 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 20. The one or more than one sensor 120 may be sampled in real time during a clamping operation by the processor 104 of the control circuit 100. The control circuit 100 receives real-time sample measurements to provide and analyze time-based information and assess, in real time, a measured parameter such as, for example, force and/or position parameters.

The one or more than one sensor 120 may comprise a strain gauge, such as a micro-strain gauge, configured to measure the magnitude of the strain in the anvil 24 during a clamped condition. The strain gauge provides an electrical signal whose amplitude varies with the magnitude of the strain. The sensors 120 may comprise a pressure sensor configured to detect a pressure generated by the presence of compressed tissue between the anvil 24 and the staple cartridge 22. The sensors 120 may be configured to detect impedance of a tissue section located between the anvil 24 and the staple cartridge 22 that is indicative of the thickness and/or fullness of tissue located therebetween.

The sensors 120 may include a force sensor 122 configured to measure forces associated with firing and/or closure conditions. For example, force sensor 122 can be at an interaction point between a closure tube and the anvil 24 to detect the closure forces applied by a closure tube to the anvil 24. The forces exerted on the anvil 24 can be representative of the tissue compression experienced by the tissue section captured between the anvil 24 and the staple cartridge 22. The force sensor 122 can be positioned at various interaction points along the closure drive system to detect the closure forces applied to the anvil 24.

Similarly, a force sensor 122 can be at an interaction point between components of the firing assembly to detect the firing forces applied by the firing assembly to advance the firing beam 60 and the sled 50 to deploy the staples into tissue and cut the tissue. The measured forces represent a firing load experienced by the firing assembly. Alternatively, or additionally, a current sensor can be employed to measure the current drawn by the motor of the motor assembly 110. The force required to advance the firing assembly corresponds to the current drawn by the motor. The measured force can be converted to a digital signal and provided to the control circuit 100.

Further to the above, the powered surgical stapling instrument 5 includes a user interface 140 having an input device (e.g., a capacitive touchscreen or a keyboard) for receiving inputs from a user and an output device (e.g., a display screen) for providing outputs to a user. Outputs can include data from a query input by the user, suggestions for products or mixes of products to use in a given procedure, and/or instructions for actions to be carried out before, during, or after surgical procedures. The user interface 140 can be in communication with the control circuit 100, as illustrated in FIG. 3.

During a surgical stapling procedure, a clinician may operate a powered surgical stapling instrument 5 to sequentially fire multiple staple cartridges along a selected tissue resection line to achieve a clinical outcome. For example, in a stomach resection procedure, the clinician may sequentially fire staple cartridges of different characteristics (e.g., size, color, type, length, staple height, staple diameter, staple size) along a selected tissue resection line to remove a portion of the stomach. The staple cartridges can be fired along the tissue resection line in an end-to-end arrangement.

The clinician may examine the tissue to be resected using any suitable imaging technique such as, for example, x-ray, registered magnetic resonance imaging (MRI), and/or computerized tomography (CT) scan. The clinician may then select a suitable tissue resection line, and staple cartridges for sequential firing along the selected tissue resection line. Visual examination, however, has its limitations, and a tissue response to stapling can vary depending on many factors including, for example, patient age, tissue health, and/or tissue type. Moreover, tissue thickness and/or stiffness may vary along the selected tissue resection line, resulting in unexpected tissue responses.

Various methods, devices, and systems are provided for adaptively adjusting operational parameters of the powered surgical stapling instrument 5 during a staple cartridge firing based on a tissue response in an earlier phase/zone of the staple cartridge firing. Moreover, various methods, devices, and systems are provided for adaptively adjusting operational parameters of the powered surgical stapling instrument 5 during a staple cartridge firing based on a tissue response in one or more previous staple cartridge firings in a surgical procedure involving multiple sequential firings.

In accordance with the present disclosure, the processor 104 can execute various program instructions, which can be stored in a memory circuit such as the memory circuit 106, to implement various algorithms associated with firing a staple cartridge by the powered surgical stapling instrument 5. Various aspects of such algorithms, e.g., thresholds, limits, triggers, conditions, pauses, wait time, are adjusted based on information learned from a tissue response in an earlier phase/zone of the staple cartridge firing, and/or based on a tissue response in one or more previous staple cartridge firings in a surgical procedure involving multiple sequential firings, as described in more detail below.

In accordance with the present disclosure, the control circuit 100 and the motor assembly 110 may have different voltage levels. The control circuit 100 may have a first voltage level that is different than the voltage of the motor assembly 110. This mitigates in transit loss of voltage or current through motor control systems of the surgical instrument. In transit loss occurs during the transit of power from the power source to the motor assembly. In accordance with the present disclosure, the motor assembly 110 may have an "H-bridge" portion that operates at a voltage level that is different than at least one other portion of the circuit. The voltage of the control circuit 100 may be higher than the voltage within the motor assembly 110 to minimize resistive losses of the transit of the power from the power source to the motor assembly. Alternatively, the voltage of the control circuit 100 may be lower than the motor assembly 110, causing higher motor efficiency.

Transmissibility improvements lead to an increase in power transfer and higher motor efficiency. In accordance with the present disclosure, power transfer can be optimized by architectural improvements. For example, a reduction of intermediate control elements within the control circuit 100 reduces overall power consumption. Distance, resistance, conductor shape, and shape all effect electrical current capacity and as a result overall power consumption. For example, resistances are between 80 mOhms to 170-200 mOhms to reduce power consumption.

In addition, parasitic losses and losses to other forms of energy, such as magnetic, capacitive, and heat, occur in the surgical instrument. Heat dissipation is a form of loss that occurs in a circuit due to proximity or enclosure constraints to other electronics. Minimization of these losses is necessary for extending battery life and efficient power transfer to the motor. With a set battery voltage the present disclosure is directed to maximizing the power delivered to the motor system. For example, the present disclosure is directed to capturing as much of the magnetic field as possible, using flux rings and running the motor at its peak spots on the motor curve. Since each cell within the battery has some internal resistance, by minimizing the current being pulled by the device, this lowers the losses caused by the internal battery resistance (heat from the battery). The cell heating can also negatively impact the battery performance.

Figure 4:
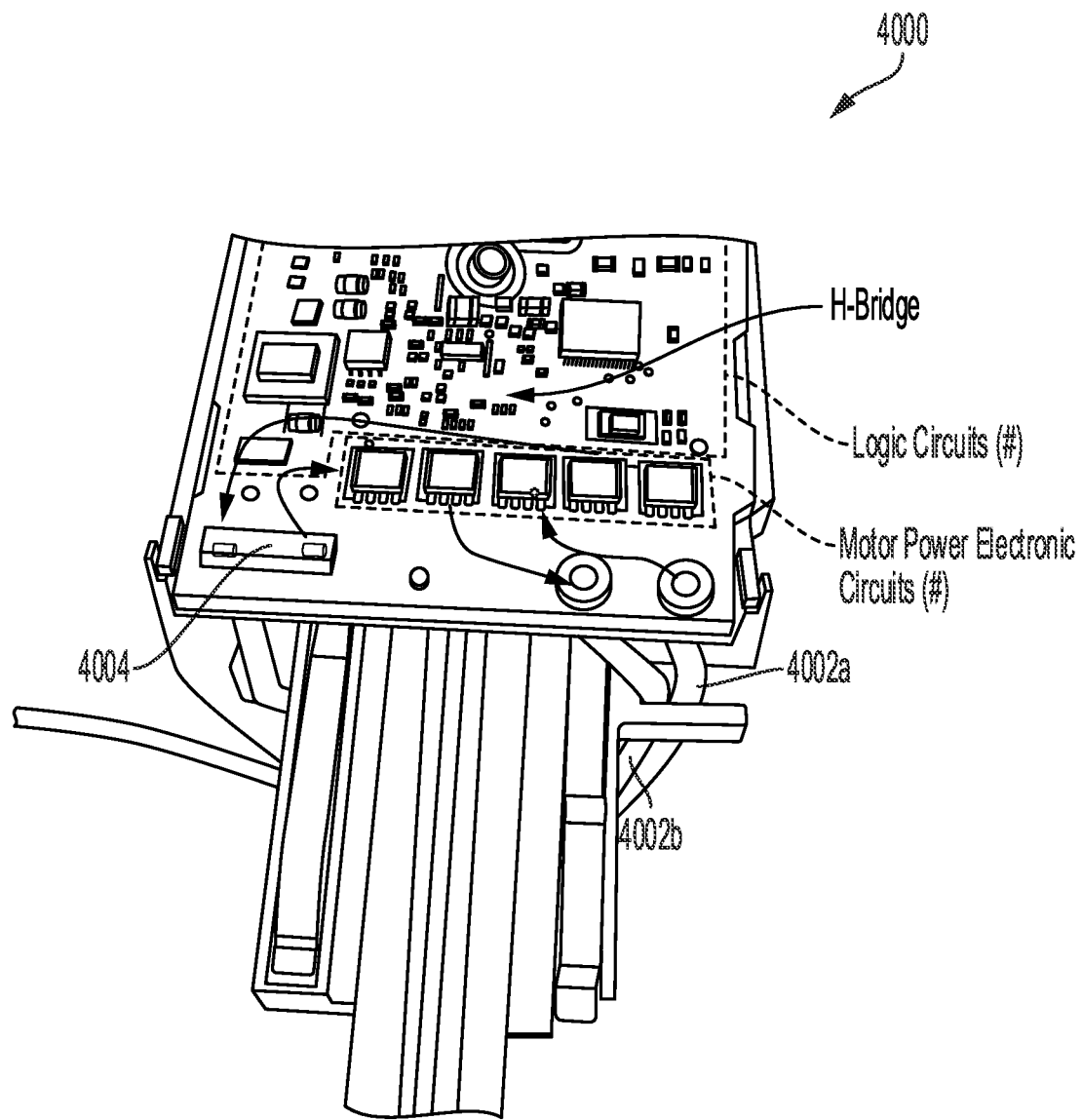
FIG. 4 is an example of a control circuit, in accordance with the present disclosure.

FIG. 4 is an example of a control circuit 4000, in accordance with the present disclosure. The control circuit 4000 is one implementation of the control circuit 100 shown in FIG. 3. As illustrated in FIG. 4, the control circuit 4000 comprises motor first and second leads 4002a, 4002b to couple the control circuit 4000 to the motor (not shown in FIG. 4, see motor 4012 in FIG. 6). In accordance with the present disclosure, the control circuit 4000 may comprise a battery 4004.

In accordance with the present disclosure, the overall current path may be minimized as the circuit components are closely spaced to minimize losses. The current path is through the positive (+) terminal of the battery 4004 to the H-Bridge, to the motor, and to the negative (−) return terminal of the battery 4004. Adjacent circuit components also lose power through induced capacitive coupling and inductive coupling.

The control circuit 4000 is disposed on a printed circuit board (PCB). On the PCB, power electronics 4001 are separated from the logic circuits 4003, such as the digital electronics or electrical conductors carrying data signals to physically and electrically isolate noisy power signal traces from digital/data traces. Accordingly, the digital traces are free from unwanted noise or interference caused by electric, magnetic, or thermal sources.

In accordance with the present disclosure, to minimize parasitic losses in the control circuit 4000, the voltage source to power the control circuit may be unpaired or decoupled from the voltage source to power the motor. This technique enables different power sources to be used. For example, a 24V battery to power a 12V motor uses a step-down circuit at the motor. The 24V battery then has less electrical losses while in storage than a 12V battery. This minimizes parasitic losses. Additional losses occur due to the skin effect in electrical conductors during pulse width modulation (PWM). For example, in electromagnetism, the skin effect refers to the tendency of an alternating electric current (AC) to become distributed within an electrical conductor such that the current density is largest near the surface of the electrical conductor and decreases exponentially with greater depths in the conductor. Thus, in AC circuits, power transfer is mostly through skin transfer while in DC circuits power transfer occurs mid-electrical conductor.

Motor efficiency is a measurement of how much of the electrical energy applied to a motor is converted to mechanical energy. Much of the remaining energy is converted into heat, which can cause a motor to burn out if the motor is operated at a torque and/or revolutions per minute (RPM) where the motor efficiency is very low. Motor heating is directly related to output torque of the motor system. Thus, it is important to control motor generated heat. One way to control motor generated heat is to use a flux ring to envelop the motor.

Figure 5:
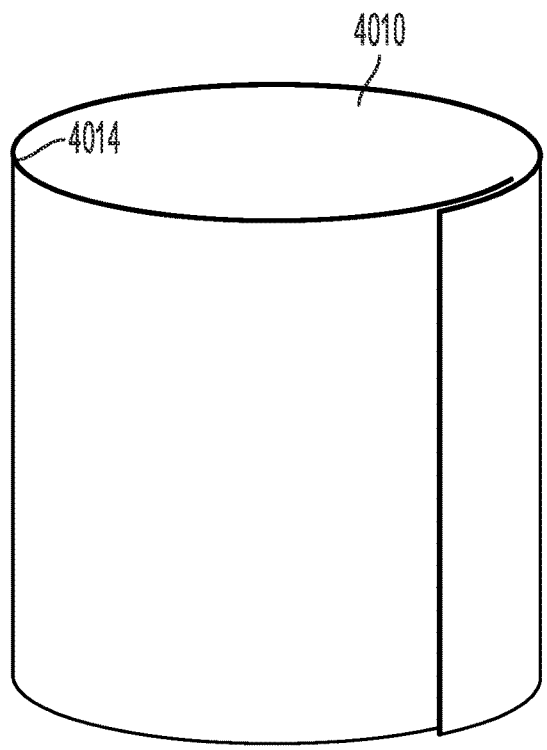
FIG. 5 is an example of a flux ring, in accordance with the present disclosure.

FIG. 5 is an example of a flux ring 4010, in accordance with the present disclosure. The flux ring 4010 is a ferrous metal ring that increases the efficiency of the magnetic field on a motor by lowering the RPM per volt and reducing the amperage draw of the motor. The flux ring 4010 also conducts additional heat away from the motor. Increasing the thickness of the flux ring 4010 enables additional heat to be conducted away from the motor.

Figure 6:
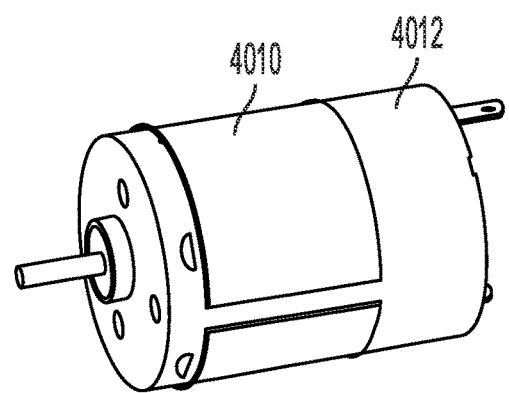
FIG. 6 is an illustration of the flux ring disposed around a motor, in accordance with the present disclosure.

FIG. 6 is an illustration of the flux ring 4010 disposed around a motor 4012, in accordance with the present disclosure. The flux ring 4010 is slidably disposed on the motor 4012. The flux ring 4010 changes the magnetic flux characteristics of the motor 4012 and impacts the performance of the motor 4012. The flux ring 4010 disposed around the motor 4012 advantageously reduces the power consumption of the motor 4012 and extends the life of the battery.

Figure 7:
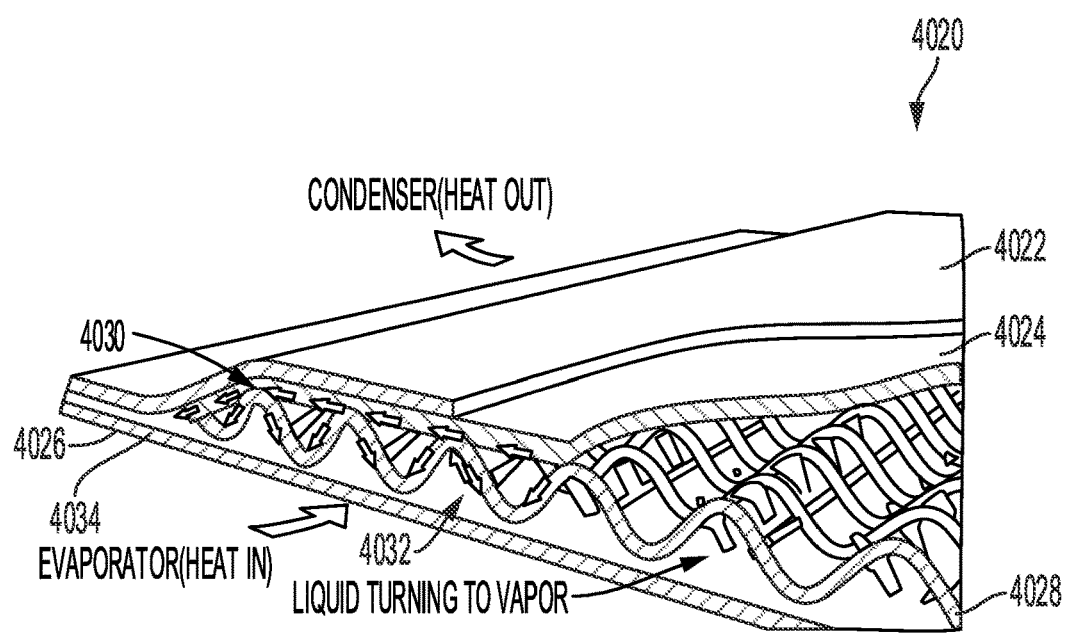
FIG. 7 illustrates a vapor chamber to remove heat from a motor, in accordance with the present disclosure.

FIG. 7 illustrates a vapor chamber 4020 to remove heat from the motor 4012, in accordance with the present disclosure. The flux ring 4010 shown in FIG. 6 may comprise the vapor chamber 4020. The vapor chamber 4020 comprises a condenser 4022, an evaporator 4026, a wick 4024 coupled to the condenser provides a liquid return path. A cavity 4032 is defined between the wick 4024 and the evaporator 4026 to accommodate fluid within the cavity 4032. Coils 4028 are disposed in the cavity 4032. The liquid returned from the wick 4024 is converted into a vapor within the cavity 4032. The evaporator 4026 is to pull heat from the motor. In accordance with the present disclosure, the evaporator 4026 may be in physical contact with the motor (not shown) from which the vapor chamber is to remove heat.

As heat is introduced to the evaporator 4026, from a motor coupling side 4034 of the vapor chamber 4020, the working fluid within the vapor chamber 4020 turns to vapor which moves to areas of lower pressure. In accordance with the present disclosure, the evaporator 4026 can be in contact with one side of the motor 4012 through the motor coupling side 4014. In another example, the evaporator 4026 is in contact with an open side of the flux ring 4010. The condenser 4022, usually a finned structure, cools the vapor such that the vapor condenses back to a liquid which is absorbed by the wick 4024 and returned via capillary action to the heat source area.

In accordance with the present disclosure, the vapor chamber 4020 can be part of the flux ring 4010 shown in FIGS. 5 and 6 to conduct heat away from the motor 4012 (FIG. 6). The vapor chamber 4020 forms a cylindrical shape. The vapor chamber 4020 may be a copper heat pipe. Further, in accordance with the present disclosure, the vapor chamber 4020 may define a shape that conforms to the outer housing or shape of a motor.

Additional techniques to minimize system parasitic losses and cool system components by removing the heat (energy) from the system components include removing heat from the H-bridge and the transistors (e.g., MOSFET devices) by way of cooling mechanisms including heat sinks, heat pipes, or vapor chambers.

Other contributing sources of heat include heat energy generated by motor vibrations when the motor is out of specification, e.g., when the motor is being operated above its operating conditions. When the motor vibrates, the motor gearbox may encounter tooth loading, which will add heat energy to the system. One solution is to optimize the impact angle for high loading conditions. During low loading conditions the efficiency is lower but it allows higher outputs during critical high loading conditions of the instrument firing process.

Another solution is to replace plastic gears with metal gears. The loading characteristics of plastic gears change the optimized or efficiency of the contact to the mating gear. The loading profile would "steal" output power due to the gear requiring more energy to rotate. If the gears are metal the contact point would not deflect which would keep the power input required lower than if plastic gears are used.

Other sources of heat energy that can be mitigated include electromagnetic interference (EMI) and electromagnetic compatibly (EMC). This includes adding effective EMI/EMC shielding and filtering to the surgical instrument to simultaneously improve EMI/EMC immunity and reduce electromagnetic emissions, while minimizing risk.

Moreover, motor efficiency can be optimized by tuning the motor drive configurations to compensate for resistance changes or losses to the power supply voltage level. One method for compensating the power supply voltage applied to the motor is through continuous control variation of one or more H-Bridge transistors by operating at least one of the transistors in the linear operating region. Operating the H-Bridge transistors in the linear region provides additional control of the current flowing to the motor. The linear region could be used to lower the current flowing to the motor, which in turn lowers the speed and reduces energy consumption that contributing to the system heat energy losses.

Figure 8:
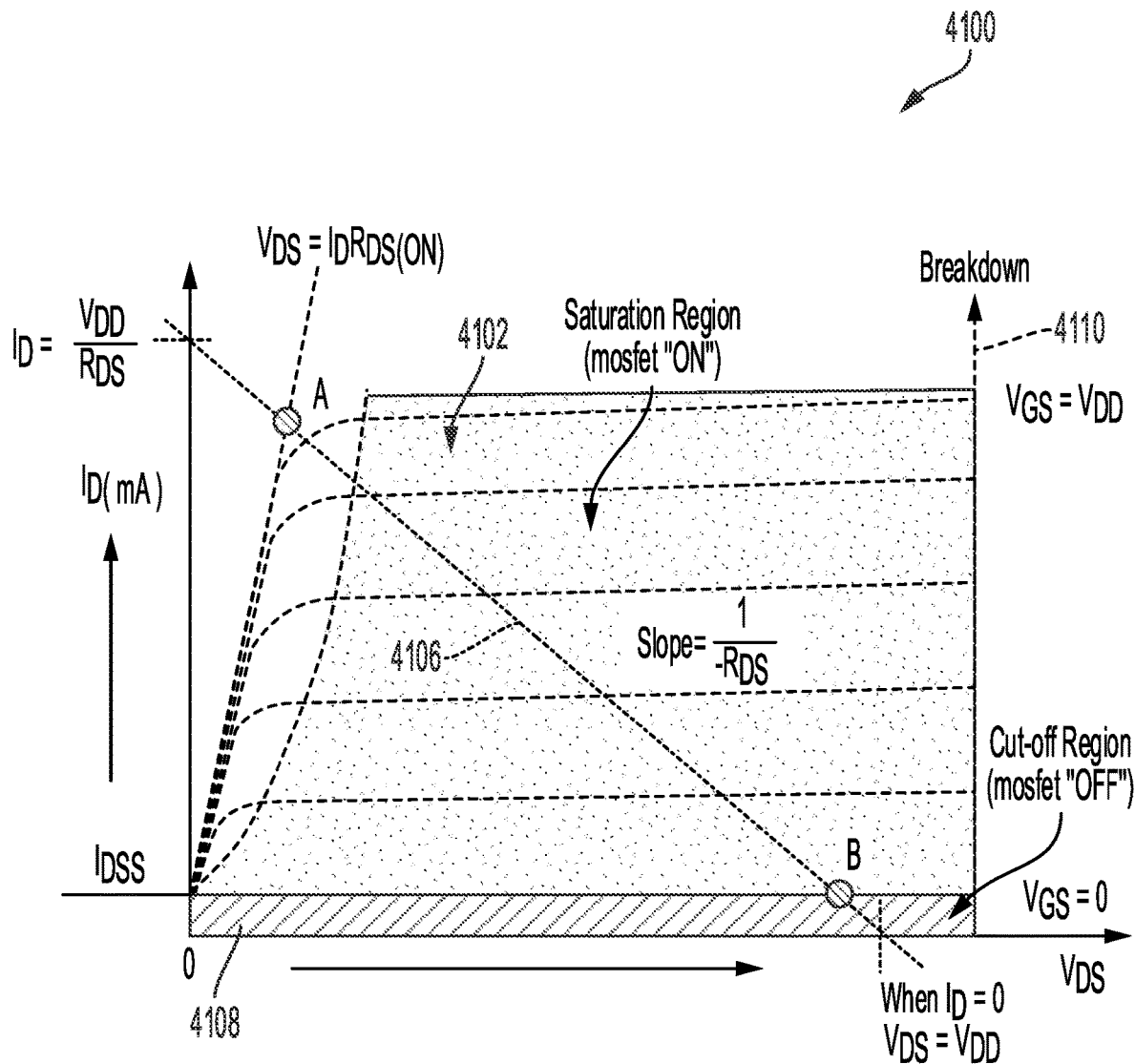
FIG. 8 is a graph 4100 illustrating characteristics of typical MOSFET devices.

Before describing techniques for operating a motorized surgical instrument, such as the powered surgical stapling instrument 5 shown in FIGS. 1-3, by operating the H-Bridge transistors in the linear region, the disclosure turns to FIG. 8. FIG. 8 is a graph 4100 illustrating characteristics of typical MOSFET devices. The graph 4100 shows Drain to Source voltage ($V_{DS}$) vs Drain Current ($I_D$) of a typical MOSFET device. The saturation region 4102 occurs when $V_{GS} > V_{TH}$ Which creates a maximum current. The load line 4106 has two points, A and B, which illustrate the voltage and current at the cut-off region and the saturation region 4102.

In the saturation region 4102, the MOSFET device will be biased so that the maximum gate voltage is applied to the MOSFET device resulting in channel resistance $R_{DS}$ being as small as possible with maximum drain current flowing through the MOSFET device. Therefore for enhancement type MOSFET devices the conductive channel is open and the device is switched "ON."

The cut-off region 4108 occurs when $V_{GS} < V_{TH}$. The MOSFET device operates as an open switch. The breakdown voltage 4110 is shown on graph 4120. By applying a suitable drive voltage to the gate of a MOSFET device, the resistance of the drain-source channel, $R_{DS(on)}$ can be varied from an "OFF-resistance" of many hundreds of kilo-Ohms, effectively acting as an open circuit, to an "ON-resistance" of less than 10, effectively acting as a short circuit.

Figure 9:
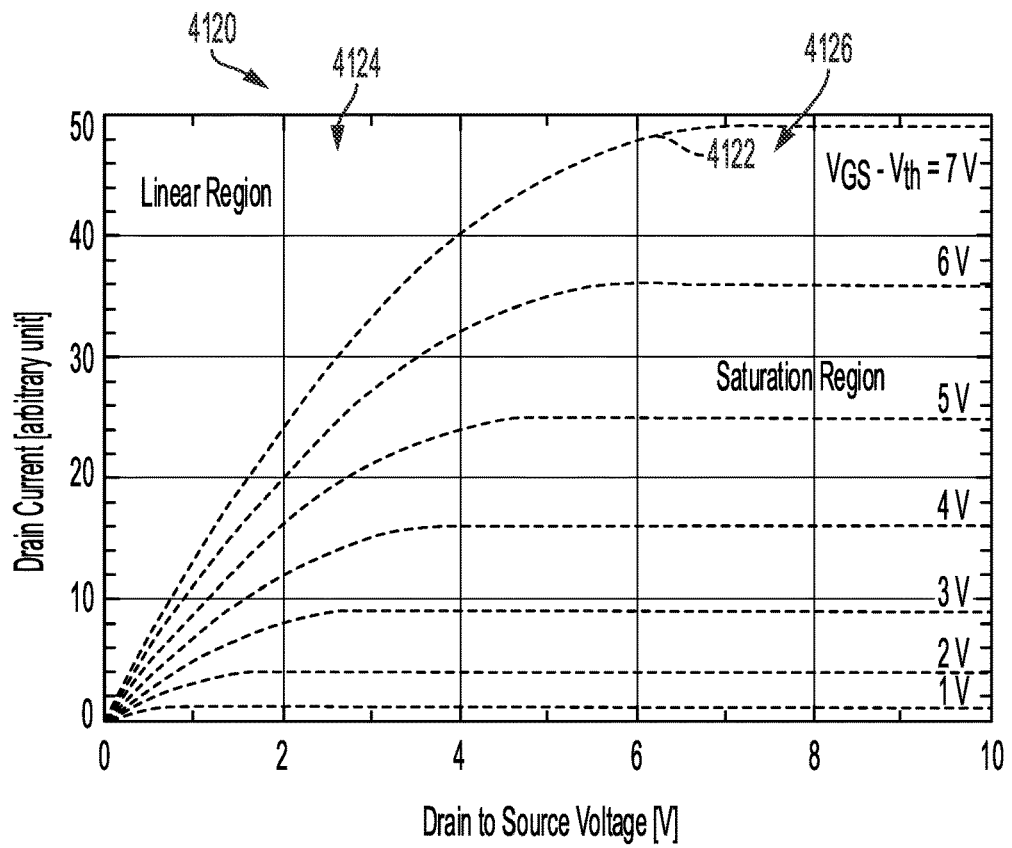
FIG. 9 illustrates a graph of characteristic Drain to Source Voltage ($V_{DS}$) vs Drain Current ($I_D$) curves for a MOSFET device operating at different values of Gate to Source Voltage ($V_{GS}$).

FIG. 9 illustrates a graph 4120 of characteristic Drain to Source Voltage ($V_{DS}$) vs Drain Current ($I_D$) curves for a MOSFET device operating at different values of Gate to Source Voltage ($V_{GS}$). The primary current flow through the MOSFET device is controlled by the voltage applied to one of the terminals rather than by a control current flow through any part of the device. When the drain voltage is increased to the saturation voltage, $V_{SAT}$ the current through the device becomes controlled solely by the gate voltage under drain saturation conditions. The linear region 4124 and saturation region 4126 are separated by the upward curving parabola 4122.

Figure 10:
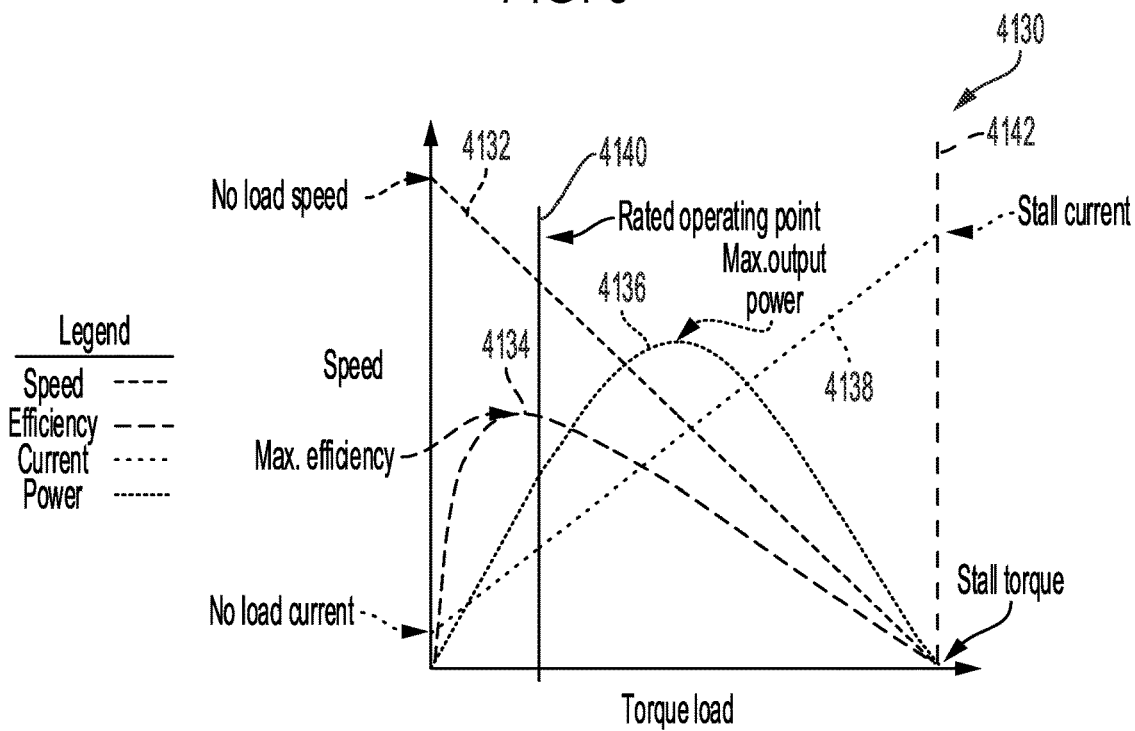
FIG. 10 is a Torque Load vs Speed graph illustrating an example of characteristics of operating a motorized surgical instrument, in accordance with the present disclosure.

FIG. 10 is a Torque Load vs Speed graph 4130 illustrating an example of characteristics of operating a motorized surgical instrument. The modulation of the current being delivered to the motor impacts the output force the motor can apply. There is a direct relationship between speed 4132 and torque.

For example, where there is no load, the speed of the motor is at a maximum. For example, when the motor is stalled 4142, there is a maximum current being applied to the motor, but no torque is being created and the rotor does not rotate while the motor is stalled. The speed and efficiency are also zero. The rated operating point is between the no load and stall conditions. The speed 4132, efficiency 4134, current 4138, and power 4136 lines all intersect the rated operating point 4140 of the motor. Rated operating point 4140 intersects all the lines for a specific load applied to the motor.

FIGS. 11-14 hereinbelow will now be described in combination with the powered surgical stapling instrument 5 and the control circuit 100 shown in FIGS. 1-3. For example, as described hereinbelow, the control circuits 4204, 4304, 4404 are example implementations of the control circuit 100 of the powered surgical stapling instrument 5 shown in FIG. 3. With reference to FIGS. 11-14 together with FIGS. 1-3, the power source 111 (FIG. 3) is divided into two circuit portions. A first portion applies power to the control circuit 100 components and a second circuit portion applies power to the motor assembly 110 (FIG. 3). In FIGS. 11-14, the two circuit portions are shown as first circuit portions 4201, 4301, 4401 and second circuit portions 4203, 4303, 4403. The first circuit portions 4201, 4301, 4401 comprises the voltage source 4202, 4302, 4402 and the control circuit 4204, 4304, 4404 and the second circuit portion 4203, 4303, 4403 comprises the motor 4210, 4310, 4410. Aspects of FIGS. 4-7 can be implemented in combination with FIGS. 11-14 to increase motor efficiency, such as a flux ring or vapor chamber disposed on the motor of FIGS. 11-14.

Figure 11:
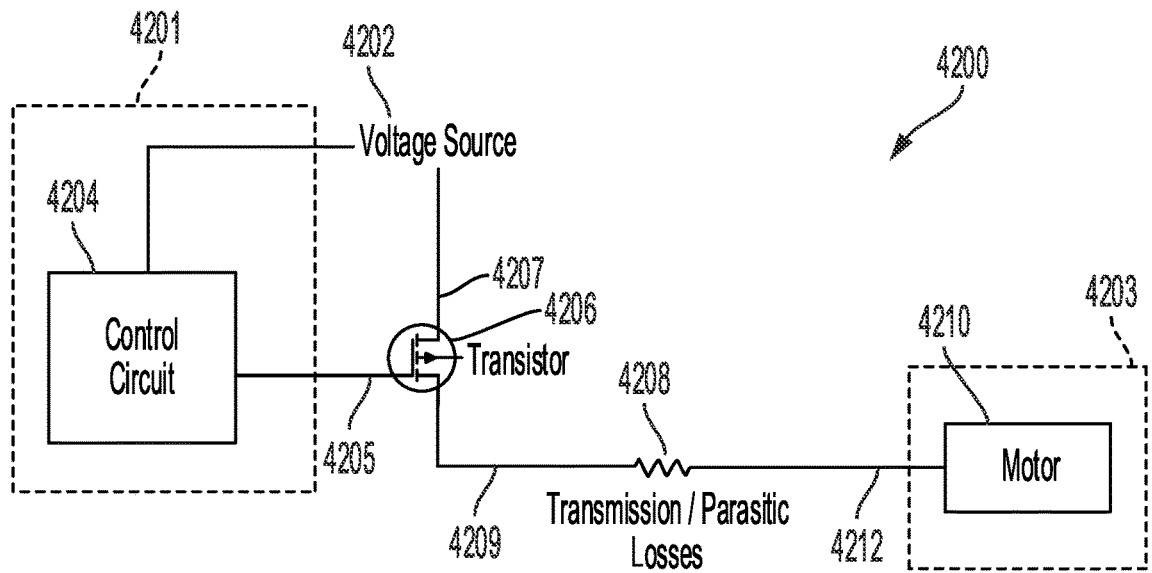
FIG. 11 is an example of a portion of a powered surgical stapler to control a motor of a powered surgical instrument, in accordance with the present disclosure.

FIG. 11 is an example of a motor control system 4200 of a powered surgical instrument to control a motor 4210 of the powered surgical instrument, in accordance with the present disclosure. The motor control system 4200 of the powered surgical instrument comprises a voltage source 4202, a transistor 4206 coupled to the voltage source 4202, and a control circuit 4204. The transistor 4206 can be a MOSFET, BJT, JFET, FET, NPN transistor, PNP transistor, or any suitable transistor. The powered surgical instrument comprises a first circuit portion 4201 operable at a first voltage level and a second circuit portion 4203 operable at a second voltage level 4212, shown as the voltage applied to the motor 4210. For example, the voltage source 4202 is configured to supply the second voltage level to the second circuit portion 4203, such that the motor receives a voltage level similar to the voltage source 4202.

In accordance with the present disclosure, the motor control system 4200 can be located within the powered surgical instrument, such as, for example, the powered surgical stapling instrument 5 shown in FIGS. 1-3. Additionally, in accordance with the present disclosure, the second voltage level 4212 can be different from the first voltage level of the voltage source 4202. The voltage source 4202 of the powered surgical instrument supplies the first voltage level to power electrical components in the first circuit portion 4201. A boost circuit (not shown) can be coupled between the voltage source 4202 and control circuit 4204 to boost the voltage level of the voltage source to the first voltage level, such that the first voltage level is higher than the voltage level of the voltage source 4202. A higher voltage to the control circuit 4204 allows the control circuit 4204 to draw less current from the voltage source 4202. This allows the motor 4210 to receive more power. A first current carrying terminal 4207 of the transistor 4206 is coupled to the voltage source 4202 and a second current carrying terminal 4209 of the transistor 4206 is coupled to the motor 4210 via transmission/parasitic losses 4208. The control circuit 4204 is coupled to the control terminal 4205 of the transistor 4206 to control the conductivity of the transistor 4206 between the first and second current carrying terminals 4207, 4209.

With reference back to FIG. 11, the transistor 4206 is to output the voltage to be applied to the motor 4210 taking into account the transmission/parasitic losses 4208. The transistor 4206 output current between the first and second current carrying terminals 4207, 4209 is controlled by the control circuit 4204 to compensate for the transmission/parasitic losses 4208.

In accordance with the present disclosure, when the voltage source 4202 is higher than the input voltage rating of the motor 4210, the control circuit 4204 may step the voltage source 4202 voltage down to a voltage usable by the motor 4210 by controlling the conductivity of the transistor 4206 between the first and second current carrying terminals 4207, 4209.

For example, in accordance with the present disclosure, the control circuit 4204 may set the transistor 4206 in the linear mode (as discussed above in connection with FIGS. 8-9) to control the output voltage of the transistor 4206 to set a current to the motor 4210 to power the motor 4210. The transistor 4206 may be located between the first and second circuit portions.

In accordance with the present disclosure, the control circuit 4204 may set the transistor 4206 in the linear mode (as discussed above in connection with FIGS. 8-9). Additionally, in accordance with the present disclosure, when the transistor 4206 is a MOSFET device, the linear mode of a MOSFET device is shown in FIGS. 8-9. Linear mode operation refers to the current saturation region in the output characteristics. The drain current ($I_{DS}$) is nearly independent of the drain to source voltage ($V_{DS}$) for a given gate to source ($V_{GS}$) voltage in the linear region. The drain current depends then directly on the $V_{GS}$ voltage of the MOSFET.

In accordance with the present disclosure, the control circuit 4204 can control the output voltage of the transistor 4206 at the second current carrying terminal 4209 of the transistor 4206 to a second voltage level by applying a stored profile to the control terminal 4205 of the transistor 4206. The stored profile stores a compensation factor to compensate for voltage drops of the voltage source 4202 during a firing operation of the powered surgical instrument driven by the motor 4210. The control circuit 4204 adjusts for the voltage drop and increases the voltage applied to the motor 4210 such that the voltage applied to the motor is similar to the voltage level of the voltage source 4202. In accordance with the present disclosure, the control circuit 4204 can set a current for the motor 4210 by controlling the control terminal 4205 of the transistor 4206 to adjust the conductivity of the transistor 4206 and apply a desired transistor voltage at the second current carrying terminal 4209 of the transistor 4206 that is compensated for the transmission/parasitic losses 4208 such that the second voltage level 4212 is suitable for efficiently operating the motor 4210 during the firing process.

In accordance with the present disclosure, any voltage drop can be 'pre-compensated' when the fire-trigger of the powered surgical instrument is activated. Pre-compensation may be based on known profiles of inrush current for a given motor 4210. For example, each powered surgical instrument includes a memory to store motor profiles. The powered surgical instruments are individually calibrated to meet a predetermined performance based on predetermined parameters. In accordance with the present disclosure, the compensation parameter values may be physically stored in a potentiometer circuit or in a memory circuit of the control circuit 4204, such as for example, an EEPROM (electrically erasable programmable read only memory). Further, in accordance with the present disclosure, the potentiometer can be controlled by the control circuit 4204 to adjust the second voltage level 4212 applied to the motor 4210. One example of a stored voltage profile during a firing operation is described below in connection with FIG. 12.

Figure 12:
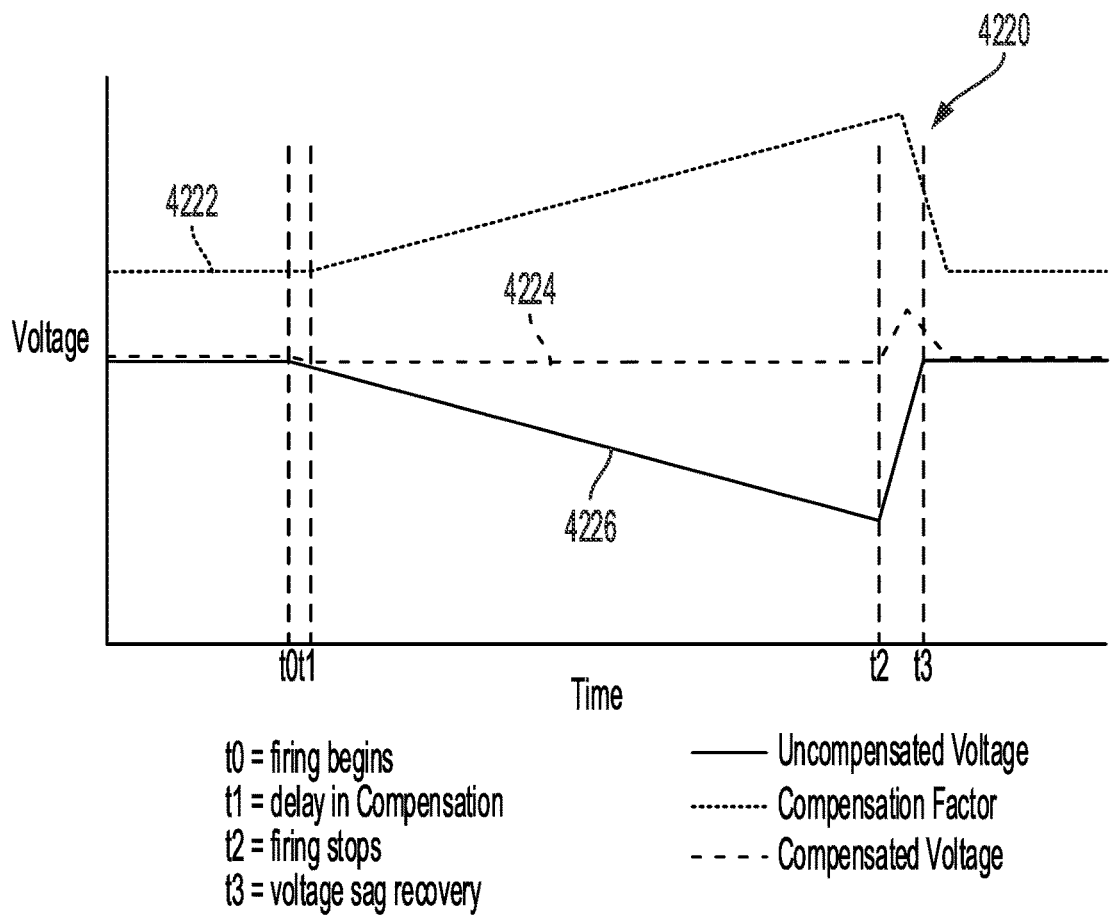
FIG. 12 is a graph illustrating an example of a stored profile of voltage during a firing stroke, in accordance with the present disclosure.

FIG. 12 is a graph 4220 illustrating an example stored profile of voltage as a function of time during a firing stroke. With reference now to FIG. 12 together with FIG. 11, the control circuit 4204 stores a profile similar to the profile depicted in the graph 4220. The control circuit 4204 adjusts the second voltage level 4212 based on a stored profile of the motor 4210. The stored profile includes the uncompensated voltage 4226, the compensation factor 4222, and the compensated voltage 4224.

To determine the profile in calibration, the second voltage level 4212 applied to the motor 4210 is measured and compared to a desired voltage to be applied to the motor 4210. A compensation factor is determined based on the difference between the applied voltage and the desired voltage. The control circuit 4204 stores the compensation factor 4222.

For example, the first circuit portion 4201 comprises the control circuit 4204 and the second circuit portion 4203 comprises the motor 4210. The transistor 4206 may separate the first circuit portion 4201 and second circuit portion 4203. The motor 4210 receives the second voltage level 4212. The control circuit 4204 receives the first voltage level. In accordance with the present disclosure, the first voltage level may be a compensated voltage, compensated by the compensation factor 4222, such that the first voltage level is higher than the second voltage level.

In accordance with the present disclosure, the first voltage level—the voltage at the voltage source 4202—may be higher than the second voltage level 4212 applied to the motor 4210. Alternatively, the first voltage level—the voltage at the voltage source 4202—may be lower than the second voltage level 4212 applied to the motor 4210.

The control circuit 4204 also minimizes or maximizes the power applied to the motor 4210 and stores algorithms to modulate the power applied to the motor 4210. For example, the first several firings of the powered surgical instrument will encounter a higher force to fire and will require more power applied to motor 4210 to advance the drive shaft 40. Based on the device cycle number, the control circuit 4204 increases the output power and monitors the power throughout the cycles. The control circuit 4204 counts the number of cycles and stores the device cycle number. The control circuit 4204 also determines the second voltage level 4212 to apply to the motor based on the stored number of cycles for the device. The control circuit 4204 also stores the output power of the prior cycles and determines a desired output power to the motor 4210, at least based in part, on prior output power.

In accordance with the present disclosure, the increase in output power from the voltage source 4202 may be controlled by changing the second voltage level 4212, e.g., the voltage applied to the motor 4210. By way of example, if the motor control system 4200 uses an 18V voltage source 4202, e.g., battery, to power the control circuit 4204 and the motor 4210, during the initial firing cycle the control circuit 4204 applies the full 18 volts to the motor 4210. As the load increases, the second voltage level 4212 applied to the motor 4210 is adjusted to the voltage necessary to complete the firing cycle. If the first several firing were at an increased load—higher than a predetermined threshold, the control circuit 4204 continues to apply the full 18 volts to the motor 4210. If the initial firings are lower than the threshold, the motor 4210 is throttled down to a lower voltage that better matches the loads on the end effector 20 (FIGS. 1 and 3). The control circuit 4204 stores the prior loads on the end effector 20 for the prior firings and determines a suitable voltage level to be applied to motor 4210 to operate properly under the loads, at least based in part on the prior loads.

In another example, during a motor 4210 stall condition, the control circuit 4204 raises the second voltage level 4212 applied to the motor 4210 incrementally to attempt to return the firing beam 60/knife (FIG. 1) without the use of a mechanical bailout. The control circuit 4204 stores differing thresholds for firing and return to minimize damage and risk. The control circuit 4204 determines the condition of the motor 4210 and determines the second voltage level 4212 to apply to the motor 4210 based on the condition of the motor 4210. In addition, the control circuit 4204 controls the decay of the H-bridge drive circuit. A slow decay of the H-bridge drive circuit increases the efficiency of the motor 4210. A faster decay allows for faster braking.

In accordance with the present disclosure, the motor 4210 may be a bipolar or unipolar stepper motor to operate outside of the pull-out and pull-in torque of the motor 4210, which causes the motor 4210 and the attached drive system to vibrate.

In accordance with the present disclosure, the transistor 4206 can be replaced with a DC/DC power converter. The DC/DC power converter drops a higher voltage provided by the voltage source 4202 down to a lower second voltage level 4212 for operating the motor 4210. In accordance with the present disclosure, the transistor 4206 may be a MOSFET device. Further, in accordance with the present disclosure, the transistor 4206 may be a BJT device.

In accordance with the present disclosure, a higher second voltage level 4212 can be utilized to drive the motor 4210, such as a 14V second voltage level 4212 for a 12V battery voltage source 4202. An unknown amount of voltage drop, such as 1V for example, will occur due to transmission/parasitic losses 4208. The transistor 4206 can then be used in the linear region to compensate the remaining overhead voltage down to second voltage level 4212 that is acceptable for the motor 4210. The control circuit 4204 controls the voltage drop of the transistor 4206 by controlling the conductivity of the transistor 4206 through the control terminal 4205.

In accordance with the present disclosure, the control circuit 4204 can monitor the voltage drop and dynamically compensates the voltage drop. The voltage drop is due to voltage and battery sag.

Figure 13:
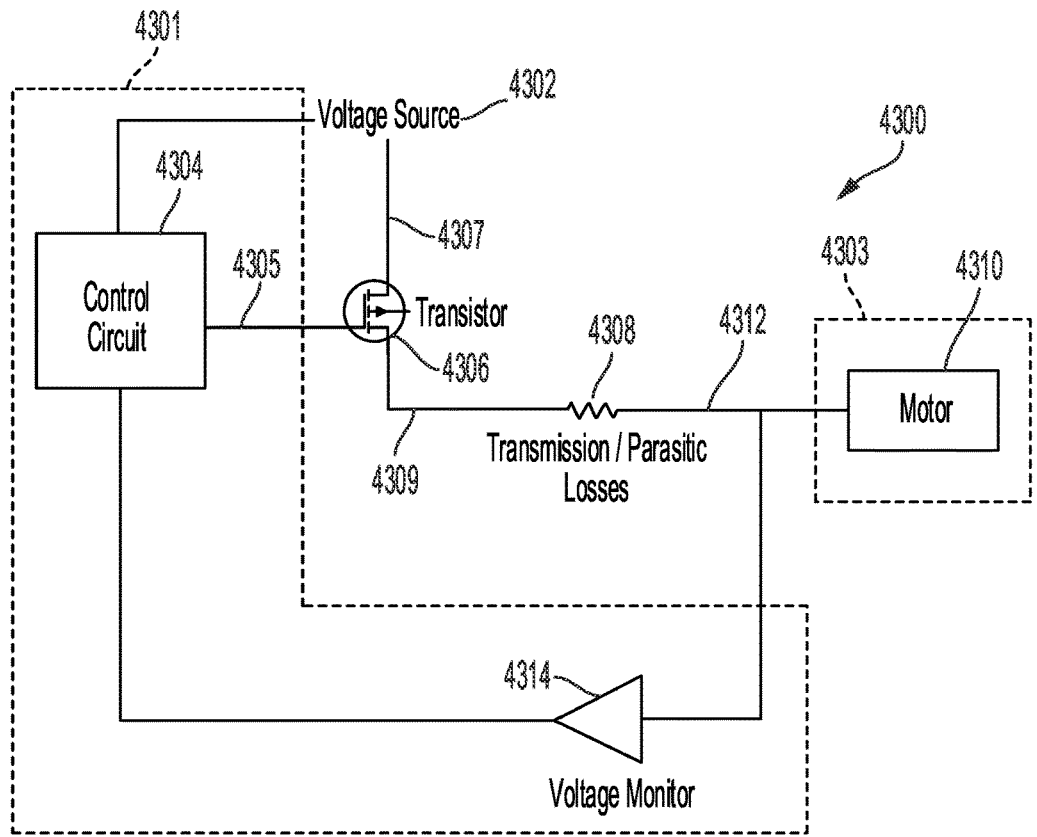
FIG. 13 is an example of a circuit to control the motor of a powered surgical stapler, in accordance with the present disclosure.
Figure 14:
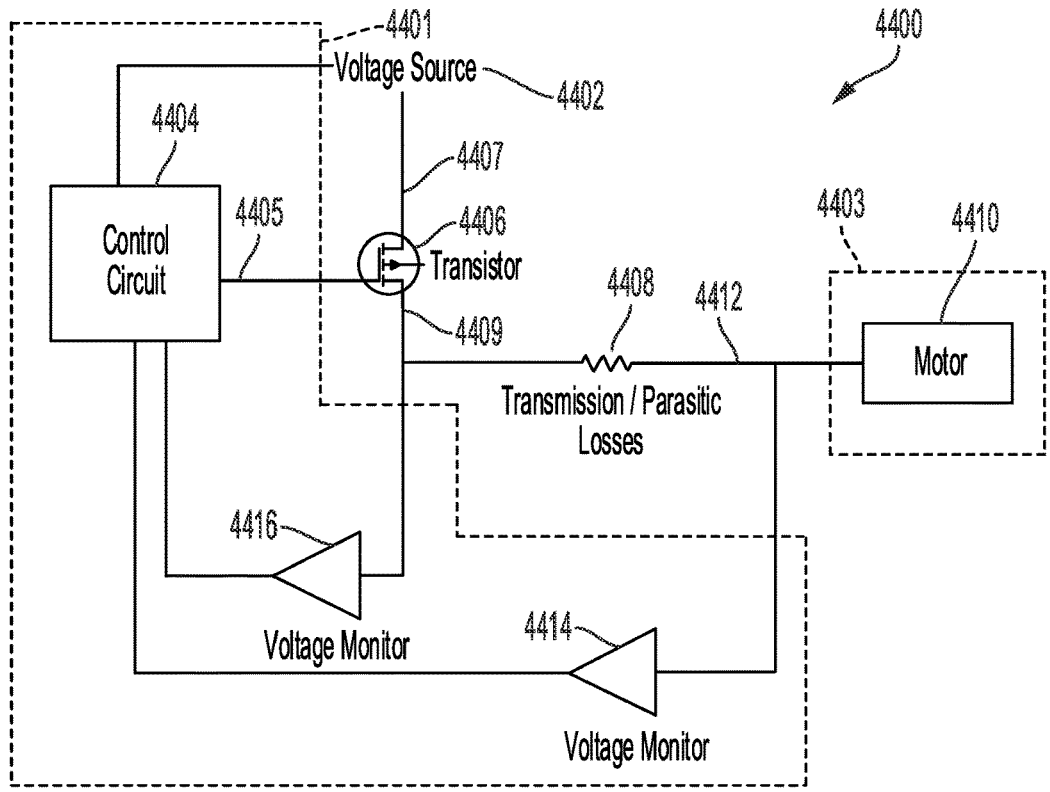
FIG. 14 is an example of a circuit to control the motor of a powered surgical stapler, in accordance with the present disclosure.

FIGS. 13 and 14 illustrate alternative implementations of the motor control system 4200 shown in FIG. 11. In accordance with the present disclosure, as illustrated in FIGS. 13 and 14, the control circuit 4304, 4404 may use an algorithm and active monitoring of the second voltage level 4312, 4412 applied to the motor 4310, 4410 to provide the status of the second voltage level 4312, 4412 being applied to the motor and to compensate the second voltage level 4312, 4412 to a desired voltage level.

With reference now to FIG. 13, there is shown a motor control system 4300 of a powered surgical instrument, in accordance with the present disclosure. The powered surgical instrument is similar to the powered surgical stapling instrument 5 shown in FIGS. 1-3. The motor control system 4300 is an example circuit implementation for controlling the motor 4310 of the powered surgical instrument. In accordance with the present disclosure, the circuits can be contained within a housing of the powered surgical instrument. The motor control system 4300 is similar to the motor control system 4200 shown in FIG. 11, and for conciseness and clarity of disclosure similar components will not be described in detail. In accordance with the present disclosure, the motor control system 4300 can be located within a housing of the powered surgical instrument. The motor control system 4300 comprises a first circuit portion 4301 operable at a first voltage level-supplied by the voltage source 4302 and a second circuit portion 4303 operable at a second voltage level 4312. In accordance with the present disclosure, the second voltage level 4312 may be different from the first voltage level supplied by the voltage source

4302. The voltage source 4302 of the powered surgical instrument supplies the first voltage level to power electronic/electrical components in the first circuit portion 4301, such as the control circuit 4304. A first conduction terminal 4307 of the transistor 4306 is coupled to the voltage source 4302. A second conduction terminal 4309 of the transistor 4306 is coupled to the motor 4310 via transmission/parasitic losses 4308. The control circuit 4304 is coupled to a control terminal 4305 of the transistor 4306.

The motor control system 4300 comprises a voltage monitor circuit 4314 coupled to the second conduction terminal 4309 of the transistor 4306, the voltage monitor circuit 4314 measures the voltage applied to the motor 4310 and provides the voltage as feedback to the control circuit 4304. In accordance with the present disclosure, the control circuit 4304 can receive the second voltage level 4312 applied to the motor 4310 as measured by the voltage monitor circuit 4314 and may adjust the second voltage level 4312 based on the measured voltage. In accordance with the present disclosure, the control circuit 4304 may compare a predetermined value of the second voltage level 4312 to the voltage applied to the motor 4310 as measured by the voltage monitor circuit 4314 and may adjust the second voltage level 4312 based on the comparison. For example, the predetermined value of the second voltage level 4312 is the voltage level of the voltage source 4302.

Compensation can also be used to allow for monitoring. Compensation can be used to allow for both unintentional losses as well as losses due to passive elements (e.g., diodes) and active elements (e.g., other active/powered circuitry).

FIG. 14 is motor control system 4400 of a surgical instrument, in accordance with the present disclosure. The powered surgical instrument is similar to the powered surgical stapling instrument 5 shown in FIGS. 1-3. The motor control system 4300 is an example circuit implementation for controlling the motor 4410 of the powered surgical instrument. The motor control system 4400 is similar to the motor control systems 4200, 4300 shown in FIGS. 11 and 13, and for conciseness and clarity of disclosure similar components will not be described in detail. In accordance with the present disclosure, the motor control system 4400 can be located within a housing of a powered surgical instrument. The motor control system 4400 comprises a first circuit portion 4401 operable at a first voltage level—supplied by the voltage source 4402 and a second circuit portion 4403 operable at a second voltage level 4412. In accordance with the present disclosure, the second voltage level 4412 may be different from the first voltage level supplied by the voltage source 4402. The voltage source 4402 of the powered surgical instrument supplies the first voltage level to power electronic/electrical components in the first circuit portion 4401, such as the control circuit 4404. A first conduction terminal 4407 of the transistor 4406 is coupled to the voltage source 4402. A second conduction terminal 4409 of the transistor 4406 is coupled to the motor 4410 via transmission/parasitic losses 4408. The control circuit 4404 is coupled to a control terminal 4405 of the transistor 4406. The motor control system 4400 comprises a first voltage monitor circuit 4414 coupled to the motor 4410 to measure the input voltage applied to the motor 4410. The voltage monitor circuit 4414 measures the voltage applied to the motor 4410. The motor control system 4400 comprises a second voltage monitor 4416 coupled to the second conduction terminal 4409 of the transistor 4406 to measure the voltage source 4402 voltage.

The differential voltage measured by the first and second voltage monitor circuits 4414, 4416 implement a current monitor to monitor the current supplied to the motor 4410. The control circuit 4404 receives a first voltage measured by the first voltage monitor circuit 4414 and a second voltage monitored by the second voltage monitor 4416 to derive a measured current to the motor 4410 and adjusts the current based on the measured current. In accordance with the present disclosure, the control circuit 4404 can monitor both current and voltage applied to the motor 4410. The control circuit 4404 stores an algorithm in memory and actively monitors both the voltage level supplied by voltage source 4402 as well as the second voltage level 4412 applied to the motor 4410 to provide the status of the current being drawn by the motor 4410. The differential voltage is measured across the transmission/parasitic losses 4408 which acts as a shunt for the purposes of monitoring current supplied to the motor 4410. This value could be characterized and calibrated during the manufacturing process against a known quantity to save the need to use a shunt resistor and therefore save costs. For example, the transmission/parasitic losses 4408 could be characterized during manufacturing and together with the differential voltage measured by the first and second voltage monitor circuits 4414, 4416 implement a current monitor to measure the current supplied to the motor 4410. The control circuit 4404 adjusts the current and voltage applied to the motor 4410 based on the monitored voltage and current.

Examples of the apparatus and method according to various aspects of the present disclosure are provided below in the following numbered clauses. An aspect of the apparatus or method may include any one or more than one, and any combination of, the numbered clauses described below.

Example 1—A powered surgical instrument, comprising a first circuit portion operable at a first voltage level, a second circuit portion (4203, 4303, 4403) operable at a second voltage level. The second voltage level is different from the first voltage level. The powered surgical instrument further comprises a voltage source (4202, 4302, 4402) to supply the first voltage level to supply power to electrical components in the first circuit portion, a transistor (4206, 4306, 4406) comprising a control terminal (4205, 4305, 4405), a first conduction terminal (4207, 4307, 4407), and a second conduction terminal (4209, 4309, 4409). The first conduction terminal (4207, 4307, 4407) is coupled to the voltage source. The powered surgical instrument further comprises a control circuit (100, 4000, 4204, 4304, 4404) coupled to the control terminal (4205, 4305, 4405) of the transistor (4206, 4306, 4406). The control circuit is to (100, 4000, 4204, 4304, 4404) set the transistor (4206, 4306, 4406) in a linear mode and control the transistor (4206, 4306, 4406) to set a current for operating a motor.

Example 2—The powered surgical instrument of Example 1, comprising a first voltage monitor circuit (4314, 4414) coupled to the motor to measure a voltage applied to the motor and wherein the control circuit is to receive the measured voltage applied to the motor and adjust the second voltage level based on the measured voltage.

Example 3—The powered surgical instrument of any of Examples 1-2, comprising a second voltage monitor (4416) coupled to the second conduction terminal (4409) of the transistor to measure a voltage at the second conduction terminal of the transistor. The control circuit is to receive the voltage measured at the second conduction terminal of the transistor and adjust the second voltage level based on the voltage measured at the second conduction terminal of the transistor.

Example 4—The powered surgical instrument of Example 3, comprising a current monitor comprising the first voltage monitor and the second voltage monitor to measure a current supplied to the motor based on a differential voltage measured by the first voltage monitor and the second voltage monitor. The control circuit is to receive the measured current supplied to the motor based on the differential voltage and adjust the current supplied to the motor based on the measured current.

Example 5—The powered surgical instrument of any of Examples 2-4, wherein the control circuit is to compare the second voltage level to the voltage applied to the motor as measured by the first voltage monitor and adjust the second voltage level based on the comparison.

Example 6—The powered surgical instrument of any of Examples 1-5, wherein the control circuit is to adjust the second voltage level based on a stored profile of the motor.

Example 7—The powered surgical instrument of any of Examples 1-6, further comprising a motor (4210, 4310, 4410).

Example 8—The powered surgical instrument of Example 7, further comprising a flux ring (4010) slidably disposed about an exterior housing of the motor.

Example 9—The powered surgical instrument of Example 8, wherein the flux ring comprises a vapor chamber (4020).

Example 10—A method comprising providing, by a voltage source (4202, 4302, 4402), a first voltage level to a first circuit portion (4201, 4301, 4401), setting, by a control circuit (100, 4000, 4204, 4304, 4404), a transistor (4206, 4306, 4406) in a linear mode, controlling, by the control circuit, the transistor to set a second voltage level to power in a second circuit portion (4203, 4303, 4403) a motor (4012, 4210, 4310, 4410), wherein the second voltage level is different from the first voltage level, and setting, by the control circuit, a current for the motor.

Example 11—The method of Example 10, further comprising measuring, by a voltage monitor circuit (4314, 4414), the voltage applied to the motor, receiving, by the control circuit, the voltage applied to the motor as measured by the voltage monitor, and adjusting, by the control circuit, the second voltage level based on the measured voltage.

Example 12—The method of Example 11, further comprising comparing, by the control circuit, the second voltage level to the voltage applied to the motor as measured by the voltage monitor, and adjusting, by the control circuit, the second voltage level based on the comparison.

Example 13—The method of any of Examples 10-12, wherein adjusting the second voltage level is based on a stored profile of the motor.

Example 14—The method of any of Examples 10-13, further comprising measuring, by a current monitor, current to the motor, receiving, by the control circuit, the measured current, and adjusting, by the control circuit, the current based on the measured current.

Example 15—The method of Example 14, comparing, by the control circuit, the current to the measured current and adjusting, by the control circuit, the current based on the comparison.

Example 16—A powered surgical instrument, comprising a first circuit portion operable at a first voltage level, a second circuit portion operable at a second voltage level, wherein the second voltage level is different from the first voltage level, a voltage source to supply the first voltage level to supply power to electrical components in the first circuit portion, a transistor comprising a control terminal, a first conduction terminal, and a second conduction terminal. The first conduction terminal is coupled to the voltage source. The powered surgical instrument comprising a control circuit coupled to the control terminal of the transistor. The control circuit is to set the transistor in a linear mode and control the transistor to set a current for operating the motor.

Example 17—The powered surgical instrument of Example 16, comprising a first voltage monitor coupled to the motor to measure a voltage applied to the motor. The control circuit is to receive the measured voltage applied to the motor and adjust the second voltage level based on the measured voltage.

Example 18—The powered surgical instrument of Example 17, comprising a second voltage monitor coupled to the second conduction terminal of the transistor to measure a voltage at the second conduction terminal of the transistor. The control circuit is to receive the voltage measured at the second conduction terminal of the transistor and adjust the second voltage level based on the voltage measured at the second conduction terminal of the transistor.

Example 19—The powered surgical instrument of Example 18, comprising a current monitor comprising the first voltage monitor and the second voltage monitor to measure a current supplied to the motor based on a differential voltage measured by the first voltage monitor and the second voltage monitor. The control circuit is to receive the measured current supplied to the motor based on the differential voltage and adjust the current supplied to the motor based on the measured current.

Example 20—The powered surgical instrument of any of Examples 17-19, wherein the control circuit is to compare the second voltage level to the voltage applied to the motor as measured by the first voltage monitor and adjust the second voltage level based on the comparison.

Example 21—The powered surgical instrument of any of Examples 16-20, wherein the control circuit is to adjust the second voltage level based on a stored profile of the motor.

Example 22—The powered surgical instrument of any of Examples 16-21, wherein the first voltage level is either higher than the second voltage level or lower than the second voltage level.

Example 23—A powered surgical instrument, comprising a motor, a first circuit portion operable at a first voltage level, a second circuit portion operable at a second voltage level. The second voltage level is different from the first voltage level. The powered surgical instrument comprising a voltage source to supply the first voltage level to power electrical components in the first circuit portion, a transistor coupled to the voltage source and the motor, a control circuit coupled to the transistor. The control circuit to control the transistor to set the second voltage level to supply power to the motor in the second circuit portion and control the transistor to set a current to the motor based on a torque of the motor.

Example 24—The powered surgical instrument of Example 23, further comprising a flux ring slidably disposed about an exterior housing of the motor.

Example 25—The powered surgical instrument of Example 24, wherein the flux ring comprises a vapor chamber.

Example 26—The powered surgical instrument of Example 25, wherein the vapor chamber comprises a condenser, an evaporator, and a wick coupled to the condenser and the evaporator, the wick defining a cavity therebetween, wherein fluid is disposed within the cavity.

Example 27—The powered surgical instrument of any of Examples 23-26,
comprising a voltage monitor coupled to the transistor and the motor. The voltage monitor to measure the voltage applied to the motor. The control circuit is to receive the voltage applied to the motor by the voltage monitor and adjust the second voltage level based on the measured voltage.

Example 28—The powered surgical instrument of any of Examples 23-27, comprising a current monitor coupled to the transistor to measure current. The control circuit is to receive the measured current and adjust the current based on the measured current.

Example 29—A method comprising: providing, by a voltage source, a first voltage level to a first circuit portion; setting, by the control circuit, a transistor in a linear mode; control, by the control circuit, the transistor to set the second voltage level to power in the second circuit portion a motor, wherein the second voltage level is different from the first voltage level; and setting, by the control circuit, a current for the motor.

Example 30—The method of Example 29, further comprising: measuring, by a voltage monitor, the voltage applied to the motor; receiving, by the control circuit, the voltage applied to the motor as measured by the voltage monitor; and adjusting, by the control circuit, the second voltage level based on the measured voltage.

Example 31—The method of Example 30, further comprising: comparing, by the control circuit, the second voltage level to the voltage applied to the motor as measured by the voltage monitor; and adjusting, by the control circuit, the second voltage level based on the comparison.

Example 32—The method of any of Examples 29-31, wherein adjusting the second voltage level is based on a stored profile of the motor.

Example 33—The method of any of Examples 29-32, further comprising: measuring, by a current monitor, current to the motor; receiving, by the control circuit, the measured current; and adjusting, by the control circuit, the current based on the measured current.

Example 34—The method of any of Examples 29-33, comparing, by the control circuit, the current to the measured current; and adjusting, by the control circuit, the current based on the comparison.

Example 35—The method of any of Examples 29-33, further comprising: providing a heat flux ring around the motor to remove heat.

The foregoing detailed description has set forth various forms of the systems and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

Any of the software components or functions described in this application, may be implemented as software code to be executed by a processor using any suitable computer language such as, for example, Python, Java, C++ or Perl using, for example, conventional or object-oriented techniques. The software code may be stored as a series of instructions, or commands on a computer readable medium, such as RAM, ROM, a magnetic medium such as a hard-drive or a floppy disk, or an optical medium such as a CD-ROM. Any such computer readable medium may reside on or within a single computational apparatus and may be present on or within different computational apparatuses within a system or network.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable of permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the present disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more than one" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more than one" or "at least one" and indefinite articles such as "a" or "an" (e.g., "a" and/or "an" should typically be interpreted to mean "at least one" or "one or more than one"); the same holds true for the use of definite articles used to introduce claim recitations. The singular form of "a", "an", and "the" include the plural references unless the context clearly dictates otherwise.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

It is worthy to note that any reference numbers included in the appended claims are used to reference exemplary embodiments/elements described in the present disclosure.

Accordingly, any such reference numbers are not meant to limit the scope of the subject matter recited in the appended claims.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material. None is admitted to be prior art.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A powered surgical instrument, comprising:
a first circuit portion operable at a first voltage level;
a second circuit portion operable at a second voltage level, wherein the second voltage level is different from the first voltage level;
a voltage source to supply the first voltage level to supply power to electrical components in the first circuit portion;
a transistor comprising a control terminal, a first conduction terminal, and a second conduction terminal, wherein the first conduction terminal is coupled to the voltage source;
a control circuit coupled to the control terminal of the transistor, the control circuit to:
set the transistor in a linear mode; and
control the transistor to set a current for operating a motor.

2. The powered surgical instrument of claim 1, comprising:
a first voltage monitor circuit coupled to the motor to measure a voltage applied to the motor; and
wherein the control circuit is to:
receive the measured voltage applied to the motor; and
adjust the second voltage level based on the measured voltage.

3. The powered surgical instrument of claim 2, comprising:
a second voltage monitor circuit coupled to the second conduction terminal of the transistor to measure a voltage at the second conduction terminal of the transistor; and
wherein the control circuit is to:
receive the voltage measured at the second conduction terminal of the transistor; and
adjust the second voltage level based on the voltage measured at the second conduction terminal of the transistor.

4. The powered surgical instrument of claim 3, comprising:
a current monitor circuit comprising the first voltage monitor circuit and the second voltage monitor circuit to measure a current supplied to the motor based on a differential voltage measured by the first voltage monitor circuit and the second voltage monitor circuit; and
wherein the control circuit is to:
receive the measured current supplied to the motor based on the differential voltage; and
adjust the current supplied to the motor based on the measured current.

5. The powered surgical instrument of claim 2, wherein the control circuit is to:
compare the second voltage level to the voltage applied to the motor as measured by the first voltage monitor circuit; and
adjust the second voltage level based on the comparison.

6. The powered surgical instrument of claim 1, wherein the control circuit is to adjust the second voltage level based on a stored profile of the motor.

7. The powered surgical instrument of claim 1, wherein the first voltage level is either higher than the second voltage level or lower than the second voltage level.

8. A powered surgical instrument, comprising:
a motor;
a first circuit portion operable at a first voltage level;
a second circuit portion operable at a second voltage level, wherein the second voltage level is different from the first voltage level;
a voltage source to supply the first voltage level to power electrical components in the first circuit portion;
a transistor coupled to the voltage source and the motor;
a control circuit coupled to the transistor, the control circuit to:
control the transistor to set the second voltage level to supply power to the motor in the second circuit portion; and
control the transistor to set a current to the motor based on a torque of the motor.

9. The powered surgical instrument of claim 8, further comprising a flux ring slidably disposed about an exterior housing of the motor.

10. The powered surgical instrument of claim 9, wherein the flux ring comprises a vapor chamber.

11. The powered surgical instrument of claim 10, wherein the vapor chamber comprises:
a condenser;
an evaporator; and
a wick coupled to the condenser and the evaporator, the wick defining a cavity therebetween, wherein fluid is disposed within the cavity.

12. The powered surgical instrument of claim 11, comprising:
a voltage monitor circuit coupled to the transistor and the motor, the voltage monitor circuit to measure the voltage applied to the motor; and
wherein the control circuit is to:
receive the voltage applied to the motor by the voltage monitor circuit; and
adjust the second voltage level based on the measured voltage.

13. The powered surgical instrument of claim 11, comprising:
a current monitor circuit coupled to the transistor to measure current; and wherein the control circuit is to:
  receive the measured current; and
  adjust the current based on the measured current.

14. A method comprising:
  providing, by a voltage source, a first voltage level to a first circuit portion;
  setting, by a control circuit, a transistor in a linear mode;
  controlling, by the control circuit, the transistor to set a second voltage level to power in a second circuit portion a motor, wherein the second voltage level is different from the first voltage level; and
  setting, by the control circuit, a current for the motor.

15. The method of claim 14, further comprising:
  measuring, by a voltage monitor circuit, the voltage applied to the motor;
  receiving, by the control circuit, the voltage applied to the motor as measured by the voltage monitor circuit; and
  adjusting, by the control circuit, the second voltage level based on the measured voltage.

16. The method of claim 15, further comprising:
  comparing, by the control circuit, the second voltage level to the voltage applied to the motor as measured by the voltage monitor circuit; and
  adjusting, by the control circuit, the second voltage level based on the comparison.

17. The method of claim 14, wherein adjusting the second voltage level is based on a stored profile of the motor.

18. The method of claim 14, further comprising:
  measuring, by a current monitor circuit, current to the motor;
  receiving, by the control circuit, the measured current; and
  adjusting, by the control circuit, the current based on the measured current.

19. The method of claim 18,
  comparing, by the control circuit, the current to the measured current; and
  adjusting, by the control circuit, the current based on the comparison.

20. The method of claim 14, further comprising:
  providing a heat flux ring around the motor to remove heat.

* * * * *